(12) United States Patent
Maliga

(10) Patent No.: US 8,143,474 B2
(45) Date of Patent: Mar. 27, 2012

(54) COMPOSITIONS AND METHODS FOR INCREASING TRANSGENE EXPRESSION IN THE PLASTIDS OF HIGHER PLANTS

(75) Inventor: Pal Maliga, East Brunswick, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 415 days.

(21) Appl. No.: 12/297,484

(22) PCT Filed: Apr. 18, 2007

(86) PCT No.: PCT/US2007/066859
§ 371 (c)(1),
(2), (4) Date: May 18, 2009

(87) PCT Pub. No.: WO2007/121467
PCT Pub. Date: Oct. 25, 2007

(65) Prior Publication Data
US 2009/0313719 A1    Dec. 17, 2009

Related U.S. Application Data

(60) Provisional application No. 60/792,853, filed on Apr. 18, 2006.

(51) Int. Cl.
*A01H 5/00* (2006.01)
*C12N 15/82* (2006.01)

(52) U.S. Cl. ..................................... 800/278; 435/320.1

(58) Field of Classification Search .......................... None
See application file for complete search history.

(56) References Cited

U.S. PATENT DOCUMENTS

| | | | |
|---|---|---|---|
| 5,545,818 A * | 8/1996 | McBride et al. ............... | 800/279 |
| 5,571,694 A | 11/1996 | Makoff | |
| 5,614,395 A | 3/1997 | Ryals | |
| 5,686,079 A | 11/1997 | Curtiss, III | |
| 5,877,402 A | 3/1999 | Maliga | |
| 6,110,736 A | 8/2000 | Hodges | |
| 6,149,919 A | 11/2000 | Domenighini | |
| 6,297,054 B1 | 10/2001 | Maliga | |
| 6,376,744 B1 | 4/2002 | Maliga | |
| 6,388,168 B1 | 5/2002 | Maliga | |
| 6,472,586 B1 | 10/2002 | Maliga | |
| 6,500,617 B1 * | 12/2002 | Stemmer et al. ................ | 506/1 |
| 6,849,778 B1 | 2/2005 | Staub | |

FOREIGN PATENT DOCUMENTS

| | | |
|---|---|---|
| EP | 0430645 | 6/1991 |
| WO | 01/21768 | 3/2001 |
| WO | 01/42509 | 6/2001 |
| WO | 01/77353 | 10/2001 |

OTHER PUBLICATIONS

Gleave et al (1998, Mol. Breeding 4:459-472).*
Gleave, A. P., et al. "Enhanced expression of the *Bacillus thuringiensis* cry9 Aa2 gene in transgenic plants by nucleotide sequence modification confers resistance to potato tuber moth." Molecular Breeding, 4: 459-472 (1998).
Chakrabarti, S. K., et al. "Expression of the cry9 Aa2 B.t. gene in tobacco chloroplasts confers resistance to potato tuber moth." Transgenic Research, 15: 481-488 (2006).
Corneille et al., Plant J., 2001, vol. 27, pp. 171-178.
Kilby et al., Trends in Gen., 1993, vol. 9, pp. 413-421.
Khan, M.S. "Fluorescent antibiotic resistance marker for tracking plastid transformation in higher plants"; Nature Biotechnology, 17: 910-915 (1999).
Dale, E.C. "Gene transfer with subsequent removal of the selection gene from the host genome", Proc. Natl. Acad. Sci. USA, 88: 10558-10562 (1991).
Srivastava, V. "Single-copy transgenic wheat generated through the resolution of complex integration patterns"; Proc. Natl. Acad. Sci. USA, 96: 11117-11121 (1999).
Le, Y. "Nuclear targeting determinants of the phage P1 Cre DNA recombinase"; Nucleic Acids Research, 27(24): 4703-4709 (1999).
Lyznik, L.A. "Activity of yeast FLP recombinase in maize and rice protoplasts"; Nucleic Acids Research, 21(4): 969-975 (1993).
Lyznik, L.A. "FLP-mediated recombination of FRT sites in the maize genome"; Nucleic Acids Research, 24(19): 3784-3789 (1996).
Zoubenko, O.V. "Efficient targeting of foreign genes into the tobacco plastid genome"; Nucleic Acids Research, 22(19): 3819-3824 (1994).
Love, J. "Stringent control of transgene expression in *Arabidopsis thaliana* using the Top10 promoter system"; The Plant Journal, 21(6): 579-588 (2000).
Serino, G. "A negative selection scheme based on the expression of cytosine deaminase in plastids"; The Plant Journal, 12(3): 697-701 (1997).
Lyznik, L.A. "Heat-inducible expression of FLP gene in maize cells"; The Plant Journal, 8(2): 177-186 (1995).
Soll, J. "Protein translocation into and across the chloroplastic envelope membranes"; Plant Molecular Biology, 38: 191-207 (1998).
Adams, D. "Cre-lox Recombination in *Escherichia coli* Cells Mechanistic Differences from the in Vitro Reaction"; J. Mol. Biol., 226: 661-673 (1992).
Craig, N.L. "The Mechanism of Conservative Site-Specific Recombination"; Annu. Rev. Genet., 22: 77-105 (1988).
Lichtenstein, C. "Prospects for reverse genetics in plants using recombination"; Plant Molecular Biology, 21: v-xii (1993).
Lubben, T.H. "Chloroplast import characteristics of chimeric proteins"; Plant Molecular Biology; 12: 13-18 (1989).
Russell, S.H. "Directed excision of a transgene from the plant genome"; Mol Gen Genet, 234: 45-59 (1992).
Timko, M.P. "Structure and Expression of Nuclear Genes Encoding Polypeptides of the Photosynthetic Apparatus"; Mol Biol of the Photosynthetic Apparatus, 381-396 (1985).
Timmermans, M.C.P. "The pFF plasmids: cassettes utilising CaMV sequences for expression of foreign genes in plants"; Journal of Biotechnology, 14: 333-344 (1990).
Wasmann, C.C. "The Importance of the transit peptide and the transported protein for protein import into chloroplasts"; Mol Gen Genet, 205: 446-453 (1986).
Gianelli et al., Infect. Immun., 1997, vol. 65, pp. 331-334.
Pizza, M. "A Genetically Detoxified Derivative of Heat-labile *Escherichia coli* Enterotoxin Induces Neutralizing . . . "; J. Exp. Med., 180: 2147-2153 (1994).

(Continued)

*Primary Examiner* — Anne Kubelik
(74) *Attorney, Agent, or Firm* — Dann, Dorfman, Herrall & Skillman; Kathleen D. Rigaut

(57) ABSTRACT

Nucleic acid constructs comprising a highly efficient 5' regulatory region for the expression of heterologous proteins from the plastids of higher plants are provided. Also provided are plant cells and transgenic plants comprising the same.

14 Claims, 4 Drawing Sheets

OTHER PUBLICATIONS

Figure 1:
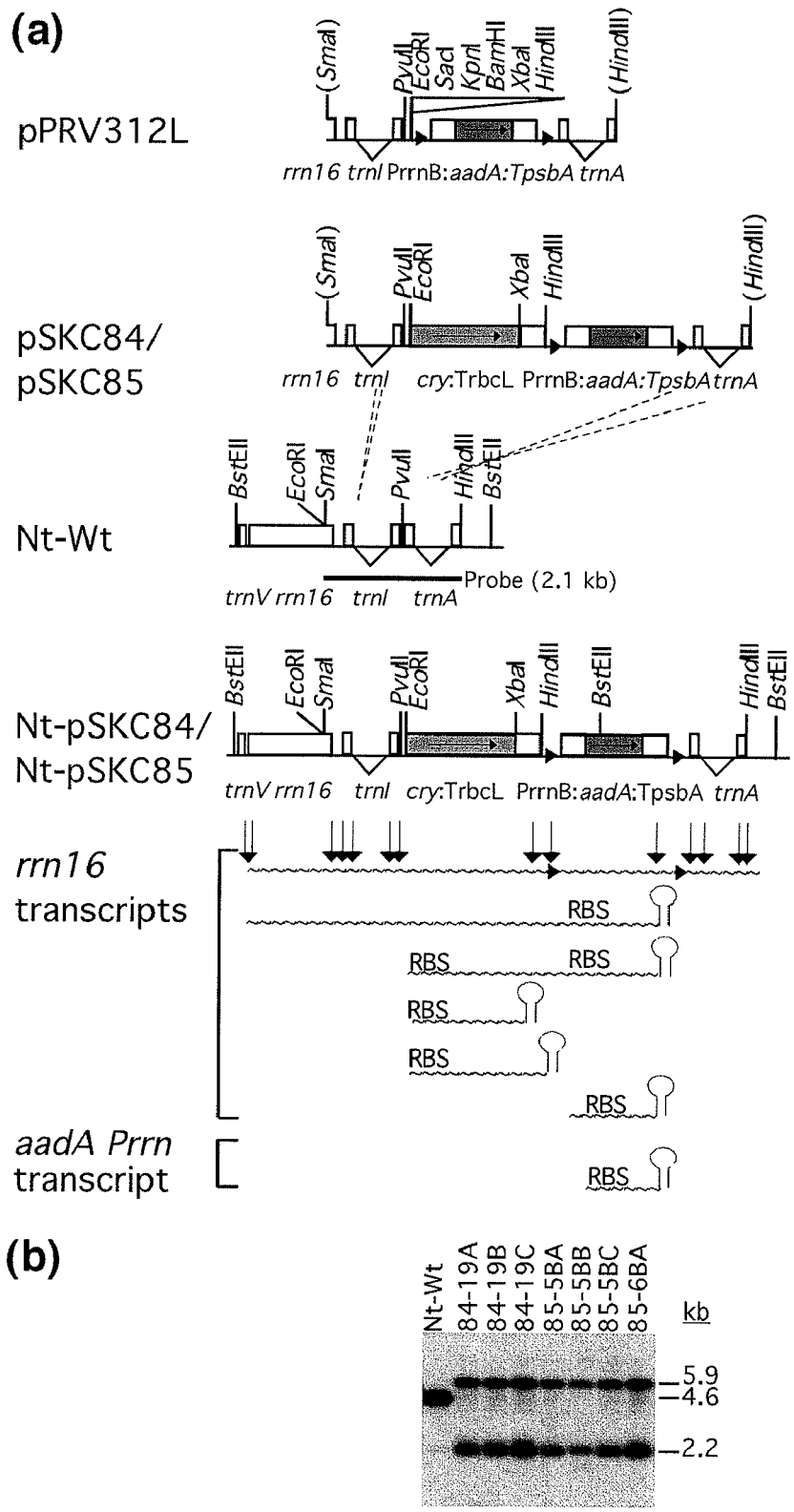

Ma, S.W. "Transgenic plants expressing autoantigens fed to mice to induce oral immune tolerance"; Nature Medicine; 3(7): 793-796 (1997).

Kuroda, H. "Complementarity of the 16S rRNA penultimate stem with sequences downstream of the AUG destabilized the plastid mRNAs"; Nucleic Acids Research, 29-4: 970-975 (2001).

Kuroda, H. "Sequences Downstream of the Translation Initiation Codon Are Important Determinants of Translation Efficiency in Chloroplasts"; Plant Phys, 125: 430-436 (2001).

Ye, G. "Plastid-expressed 5-enolpyruvylshikimate-3-phosphate synthase genes provide high level glyphosate tolerance in tobacco"; The Plant Journal, 25(3): 261-270 (2001).

Staub, J.M. "High-yield production of human therapeutic protein in tobacco chloroplasts"; Nature Biotechnology, 18: 333-338 (2000).

Heifetz, P.B. "Genetic engineering of the chloroplast"; Biochimie, 82: 655-666 (2000).

Giddings, G. "Transgenic plants as factories for biopharmaceuticals"; Nature Biotechnology, 18: 1151-1155 (2000).

Douce, G. "Genetically Detoxified Mutants of Heat-Labile Toxin from *Escherichia coli* Are Able to Act as Oral Adjuvants"; Infection and Immunity, 67(9): 4400-4406 (1999).

Douce, G. "Mucosal immunogenicity of genetically detoxified derivatives of heat labile toxin from *Escherichia coli*"; Vaccine, 16(11/12): 1065-1073 (1998).

Barchfeld, G.L. "The adjuvants MF59 and LT-K63 enhance the mucosal and systemic immunogenicity of subunit influenza vaccine administered in mice"; Vaccine, 17: 695-704 (1999).

Carrier, H. "Kanamycin resistance as a selectable marker for plastid transformation in tobacco"; Mol Gen Genet, 241: 49-56 (1993).

Hajdukiewicz, P. "Multiple pathways for Cre/lox-mediated recombination in plastids" The Plant Journal, 27(2): 161-170 (2001).

Daniell, H. "Marker free transgenic plants: engineering the chloroplast gene without the use of antibiotic selection" Curr. Genet., 39: 109-116 (2001).

Tacket, C. "Immunogenicity in humans of a recombinant bacterial antigen delivered in a transgenic potato" Nature Medicine, 4(5): 607-609 (1998).

Tacket, C. "A review of oral vaccination with transgenic vegetables" Microbes and Infection, 777-783 (1999).

Tregoning, J. "Expression of tetanus toxin Fragment C in tobacco chloroplasts" Nucleic Acids Research, 31(4): 1174-1179 (2003).

Bock, R. "Transgenic Plastids in Basic Research and Plant Biotechnology" J. Mol. Biol., 312: 425-438 (2001).

Magagnoli, C. "Mutations in the A Subunit Affect Yield, Stability, and Protease Sensitivity of Nontoxic Derivatives . . . " Infection and Immunity, 64(12): 5434-5438 (1996).

Ebinuma. "Systems for the removal of a selection marker and their combination with a positive marker." Paint Cell Rep. 2001;20:383-392.

Beuning, L.L., et al. "Minor modifications to the cry1Ac9 nucleotide sequence are sufficient to generate transgenic plants resistant to *Phthorimaea operculella*." Annals of Applied Biol. 2001;138:281-292. [Abstract].

Ebora, et al. "Transgenic Potato Expressing the *Bacillus thuringiensis* CryIA(c) Gene Effects on the Survival and Food Consumption of *Phthorimea operculella* (Lepidoptera: Gelechiidae) and *Ostrinia nubilalis* (Lepidoptera: Noctuidae)."Journal of Economic Entomology, vol. 87, No. 4, Aug. 1994, pp. 1122-1127(6) [Abstract].

Jansens, et al. "*Phthorimaea operculella* (Lepidoptera: Gelechiidae) Resistance in Potato by Expression of the *Bacillus thuringiensis* CryIA(b) Insecticidal Cry~tal Protein." Journal of Economic Entomology, vol. 88, No. 5, Oct. 1995, pp. 1469-1476(8). [Abstract].

* cited by examiner

COMPOSITIONS AND METHODS FOR INCREASING TRANSGENE EXPRESSION IN THE PLASTIDS OF HIGHER PLANTS

The present application is §371 application of PCT/US2007/066859 filed 18 Apr. 2007 which claims priority to US Provisional Application No. 60/792,853 filed 18 Apr. 2006, the entire disclosure of each being incorporated by reference herein.

FIELD OF THE INVENTION

This invention relates to the fields of molecular biology and the expression of transgenes in the plastids of higher plants. More specifically, the invention provides DNA constructs, and vectors for enhancing the expression level of transgenes encoding proteins having commercial or therapeutic applications. Also provided are transgenic plants comprising such DNA constructs and vectors.

BACKGROUND OF THE INVENTION

Several publications and patent documents are cited throughout this application in order to better describe the state of the art to which this invention pertains. Each of these citations is incorporated by reference herein.

Potato tuber moth (*Phthorimaea operculella*, Lepidoptera, Gelechiidae) is one of the most destructive insect pests of potato with a pandemic distribution. In the field, the moths lay their eggs on the potato foliage and the larvae mine the foliage and the stems. Larvae attack the tubers through infected stems or may enter the tubers directly. Development of cultivars resistant to potato tuber moth through conventional breeding has not been successful because of lack of reliable resistance sources in potato germplasm. However, considerable degree of protection has been achieved by using insecticidal crystal proteins of the soil bacterium *Bacillus thuringiensis* (B.t.). Insecticidal crystal proteins are susceptible to UV damage necessitating frequent sprays on the standing crop. To overcome this, transgenic potato lines with tuber moth resistance have been developed by engineering cry1 class B.t. genes. Transgenic potato lines with variable level of PTM resistance have been obtained by expressing the native cry1Aa (Chan et al., 1996), cry1Ab (Jansens et al., 1995) and cry1Ac (Ebora et al., 1994) genes. Nuclear transformation with native cry genes in plants, however, results in very low levels of B.t. protein expression due to instability of prokaryotic transcripts in plant systems (Murray et al., 1991). Relatively high level of B.t. protein expression with better PTM control could be achieved by using codon modified and truncated cry1Ac9 (Beuning et al., 2001; Davidson et al., 2002), cry 1Ia1 (Mohammed et al., 2000; Douches et al., 2002), and a hybrid Bt toxin (SN19) gene consisting of domain I and III of cry1Ba and domain II of cry1Ia (Naimov et al., 2003). Gleave et al. cloned and sequenced a B.t. gene, later named cry9Aa2, from *Bacillus thuringiensis* var. *galleriae* (strain DSIR517) that showed strong insecticidal activity to *P. operculella* ($LC_{50}$ 80 ng/ml) (Gleave et al., 1992). The amino acid sequence of this new B.t. protein was significantly different from those belonging to Cry1 class and, therefore, it was placed under the new class of Cry9 (Crickmore et al., 1998). In their later work, Gleave et al. transformed tobacco with the native and the modified versions of the cry9Aa2 gene and found significant improvement in B.t. expression as well as PTM resistance in those expressing the truncated and codon modified versions (Gleave et al., 1998). It is apparent from the published work that sequence modification of cry nuclear genes is an essential requirement for achieving satisfactory levels of toxin expression and PTM control in transgenic plants.

SUMMARY OF THE INVENTION

In accordance with the present invention, the Cry9Aa2 crystal protein gene has been expressed in plastids and high levels of protein production obtained. Expression of transgenes in plastids involves placing the coding segment under control of prokaryotic-type plastid expression signals and incorporating the transgene into the plastid genome by homologous recombination events via plastid targeting sequences. There are 1,000 to 10,000 identical copies of the circular, double-stranded plastid genome ~150-kb in size. Uniform alteration of all genome copies is obtained by selective amplification of transformed copies and gradual loss of non-transformed copies during plant regeneration on a selective tissue culture medium (Bock & Khan, 2004; Maliga, 2004). Expression of B.t. insecticidal protein genes in the plastid genome was found useful to obtain high protein levels of cry1Ac (McBride et al., 1995), cry2Aa2 (Kota et al., 1999; De Cosa et al., 2001) and cry1Ia5 (Reddy et al., 2002) from native bacterial genes without a reported impact on plant fitness or imposing a yield penalty. We report here that expression of the cry9Aa2 gene also results in high expression levels, ~10% of the total soluble cellular protein and ~20% in the membrane fraction, and conferred resistance in feeding trials to potato tuber moth. However, unlike in the earlier cases, we also found that high Cry9Aa2 expression levels significantly delayed plant development, yet fully developed plants were indistinguishable from wild type.

Thus, a preferred embodiment of the invention comprises a nucleic acid construct comprising in the 5' to 3' direction, a 5' nucleic acid sequence comprising a 49 nucleotide segment of the native cry9aA2 5'-UTR; b) a nucleic acid sequence encoding a heterologous protein or polypeptide of interest; and c) a transcription termination region, said construct optionally further comprising a nucleic acid encoding a selectable marker. The construct may optionally comprise flanking homologous sequences obtained from the plastid genome which facilitate homologous recombination into said genome. In a particularly preferred embodiment, the 49 nucleotide segment comprises SEQ ID NO: 4.

The constructs of the invention can also comprise sequences encoding heterologous proteins of interests. Such proteins include, without limitation, antibodies, hormones, interferons, bacterial toxins, viral proteins, cytokines, proinsulin, antimicrobial peptides, insecticidal proteins, and enzymes suitable for the production of polyhydroxybutyrate (polyhydroxyalkanoate) polymers. Also included in the invention are plant cells and transgenic plants obtained therefrom comprising the constructs described above.

BRIEF DESCRIPTION OF THE DRAWINGS

FIG. 1. Introduction of the cry9Aa2 gene into the tobacco plastid genome. (A) Map of the plastid-targeting region in plastid vector pPRV312L and cry9Aa2 vectors pSKC84 (Cry9Aa2 not tagged) and pSKC85 (Cry9Aa2 c-myc tagged) and of the cognate regions in the wild-type (wt) and transplastomic plants. Map positions are shown for: the cry9Aa2 gene; aadA, the selectable spectinomycin resistance gene; rrn16, trnI and trnA plastid genes. Wavy lines symbolize transcripts; vertical arrows above the line mark processed ends; triangles indicate loxP sites; RBS, marks position of ribosome binding site. Map position of the 2.1-kb EcoRI-HindIII probe is also shown. (B) DNA gel blot confirms cry9Aa2 integration in the tobacco plastid genome. Data are shown for transplastomic lines transformed with plasmids pSKC84 and pSKC85 and the wild-type parental line. BstEII digested total cellular DNA was probed with the 2.1-kb EcoRI-HindIII ptDNA fragment to detect the wild type (4.6 kb) and transgenic (5.9 kb and 2.2 kb) BstEII fragments.

Figure 2:
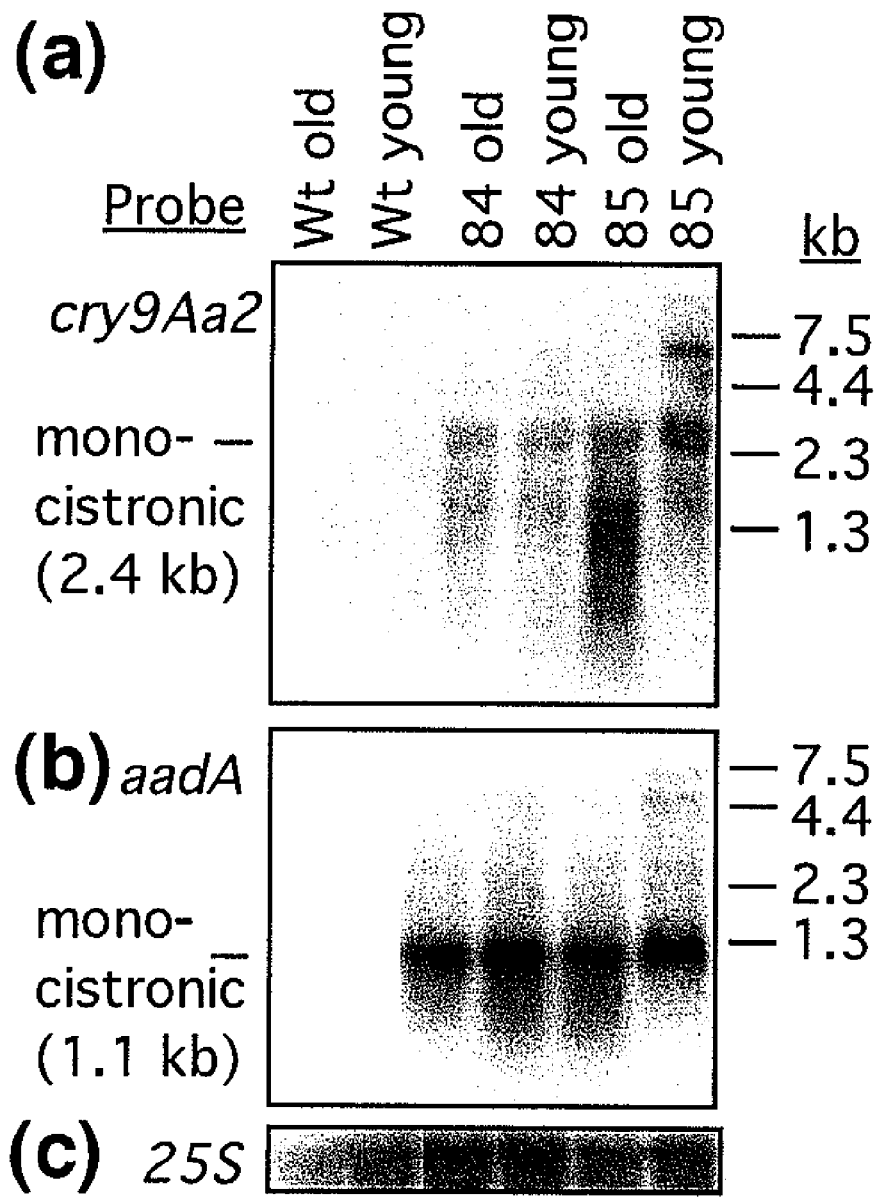

FIG. 2. Testing mRNA accumulation by probing total cellular RNA with (A) cry9Aa2 (1.3-kb SwaI fragment), (B) aadA (0.8-kb NcoI-XbaI fragment) and (C) cytoplasmic 25S rRNA (loading control) probes.

Figure 3:
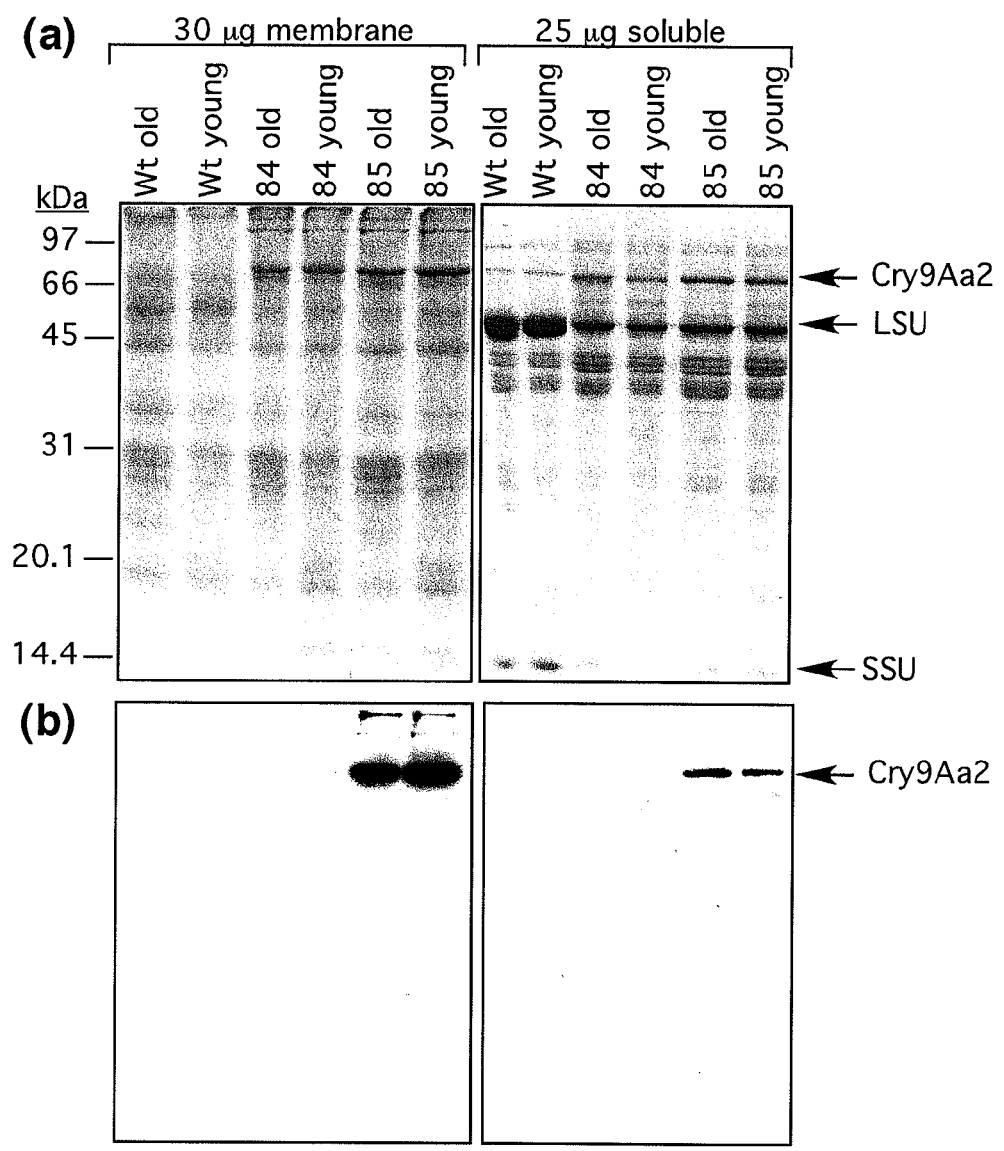

FIG. 3. Cry9Aa2 protein accumulation in tobacco leaves. (A) Soluble (25 µg per lane) and membrane protein (30 µg per lane) fractions were separated by SDS-PAGE and stained with Coomassie blue R250. The position of Cry9Aa2 and the large (LSU) and small (SSU) rubisco subunits are marked by arrows. (B) The c-myc antibody recognizes the tagged Cry9Aa2 protein in Nt-pSKC85 extracts.

FIG. 4. The transplastomic Nt-pSKC84 and Nt-pSKC85 plants. (A) Expression of Cry9Aa2 gene delays development of transplastomic plants. Shown are one-month old seedlings. (B) Potato tuber moth bioassay on detached transplastomic tobacco leaves expressing the Cry9Aa2 crystal protein. All larvae died on the leaves of transplastomic tobacco lines Nt-pSKC84-19CA and Nt-pSKC85-5BA.

DETAILED DESCRIPTION OF THE INVENTION

We report here the control of potato tuber moth (*Phthorimaea operculella*) by incorporating a truncated *Bacillus thuringiensis cry*9Aa2 gene in the plastid genome. Plasmids pSKC84 and pSKC85 are derivatives of a new polycistronic plastid transformation vector, pPRV312L, that carries spectinomycin resistance (aadA) as a selective marker and targets insertions in the trnI-trnA intergenic region. The Cry9Aa2 N-terminal region (82.1 kDa; 734 amino acids) was expressed in a cassette, which consists of 49 nucleotides of the cry9Aa2 leader and the 3'-untranslated region of the plastid rbcL gene (TrbcL), and relies on readthrough transcription from the plastid rRNA operon. In a tobacco leaf bioassay, expression of Cry9Aa2 conferred resistance to potato tuber moth. In accordance, the Cry9Aa2 insecticidal protein accumulated to high levels, ~10% of the total soluble cellular protein and ~20% in the membrane fraction. However, high-level Cry9Aa2 expression significantly delayed plant development. Thus, a practical system to control potato tuber moth by Cry9Aa2 expression calls for down-regulation of its expression.

The following definitions are provided to facilitate an understanding of the present invention:

Heteroplastomic refers to the presence of a mixed population of different plastid genomes within a single plastid or in a population of plastids contained in plant cells or tissues.

Homoplastomic refers to a pure population of plastid genomes, either within a plastid or within a population contained in plant cells and tissues. Homoplastomic plastids, cells or tissues are genetically stable because they contain only one type of plastid genome. Hence, they remain homoplastomic even after the selection pressure has been removed, and selfed progeny are also homoplastomic. For purposes of the present invention, heteroplastomic populations of genomes that are functionally homoplastomic (i.e., contain only minor populations of wild-type DNA or transformed genomes with sequence variations) may be referred to herein as "functionally homoplastomic" or "substantially homoplastomic." These types of cells or tissues can be readily purified to a homoplastomic state by continued selection.

Plastome refers to the genome of a plastid.

Transplastome refers to a transformed plastid genome.

Transformation of plastids refers to the stable integration of transforming DNA into the plastid genome that is transmitted to the seed progeny of plants containing the transformed plastids. Alternatively, transformation may also include the introduction and transient expression of heterologous DNA into the plastid or nuclear genomes.

Selectable marker gene refers to a gene that upon expression confers a phenotype by which successfully transformed plastids or cells or tissues carrying the transformed plastid can be identified.

Transforming DNA refers to homologous DNA, or heterologous DNA flanked by homologous DNA, which when introduced into plastids becomes part of the plastid genome by homologous recombination.

An alternative type of transforming DNA refers to a DNA which contains recombination site sequences for a site-specific recombinase or integrase. Insertion of this type of DNA is not dependent of the degree of homology between the transforming DNA and the plastid to be transformed but rather is catalyzed by the action of the recombinase or integrase on the first and second recombination sites.

"Operably linked" refers to two different regions or two separate genes spliced together in a construct such that both regions will function to promote gene expression and/or protein translation.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "vector" is a replicon, such as a plasmid, cosmid, bacmid, phage or virus, to which another genetic sequence or element (either DNA or RNA) may be attached so as to bring about the replication of the attached sequence or element. Vectors, expression cassettes and methods suitable for the generation of transplastomic plants are described in U.S. Pat. Nos. 6,624,296, 6,472,586, 6,388,168, 6,376,744, 6,297,054, 5,877,402, and 5,451,513, by Maliga et al., the disclosures of which are incorporated by reference herein.

An "expression operon" refers to a nucleic acid segment that may possess transcriptional and translational control sequences, such as promoters, enhancers, translational start signals (e.g., ATG or AUG codons), elements which regulate mRNA stability, processing and translation, terminators, and the like, and which facilitate the production of a polypeptide coding sequence in a host cell or organism. Such expression signals may be combined such that production of said polypeptide occurs transiently or is produced stably over the life of the cell.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application.

Amino acid residues described herein are preferred to be in the "L" isomeric form. However, residues in the "D" isomeric form may be substituted for any L-amino acid residue, provided the desired properties of the polypeptide are retained. All amino-acid residue sequences represented herein conform to the conventional left-to-right amino-terminus to carboxy-terminus orientation The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion, biolistic bombardment and the like.

"Agroinfiltration" refers to Agrobacterium mediated DNA transfer. Specifically, this process involves vacuum treatment of leaf segments in an Agrobacterium suspension and a subsequent release of vacuum which facilitates entry of bacterium cells into the inter-cellular space.

"T-DNA" refers to the transferred-region of the Ti (tumor-inducing) plasmid of Agrobacterium tumefaciens. Ti plasmids are natural gene transfer systems for the introduction of heterologous nucleic acids into the nucleus of higher plants. Binary Agrobacterium vectors such pBIN20 and pPZP22 (GenBank Accession Number 10463) are known in the art.

A "plastid transit peptide" is a sequence which, when linked to the N-terminus of a protein, directs transport of the protein from the cytoplasm to the plastid.

A "clone" or "clonal cell population" is a population of cells derived from a single cell or common ancestor by mitosis.

A "cell line" is a clone of a primary cell or cell population that is capable of stable growth in vitro for many generations.

The materials and methods set forth below were utilized in the performance of Example I.

Construction of Transformation Vectors

Plastid transformation vector pPRV312L targets insertions in the trnI/trnA intergenic region in the plastid ribosomal RNA operon (GenBank Accession Number DQ489715, SEQ ID NO: 1). Vector pPRV312L is a pUC118 plasmid derivative in which the PvuII fragment was replaced with the SmaI-HindIII tobacco ptDNA fragment (nucleotides 104,093-106, 202; GenBank Accession No. Z00044) (Shinozaki et al., 1986). The polycloning site and marker gene were introduced as a PvuII-SacI (blunted with T4 DNA polymerase) fragment. The aadA marker gene is expressed in a cassette consisting of the PrrnLatpBDB promoter (Kuroda & Maliga, 2001a) and TpsbA, the 3'-UTR of psbA gene (Shinozaki et al., 1986). The aadA gene is flanked by the P1 phage loxP sites to facilitate its excision by the CRE site-specific recombinase (Corneille et al., 2001; Lutz et al., 2006).

Plasmid pNZA10 carrying the cry9Aa2 gene (GenBank Accession number X58534) was obtained from the Bacillus Genetic Stock Center, The Ohio State University, Columbus, Ohio. First the HincII/BamH1 fragment (2.2 Kbp) encoding 49 nucleotides of the leader sequence and the N-terminal half of the cry9Aa2 gene was excised from plasmid pNZA10 and sub-cloned into a pBluescriptKS (Stratagene, La Jolla, Calif.) plasmid. The C-terminally truncated cry9Aa2 gene was converted into an EcoRI-XbaI fragment for expression in pPRV312L. The XhoI site upstream of the HincII was converted into an EcoRI site by blunting and linker ligation and an in-frame stop codon was introduced in a BamHI-XbaI linker (5'-GGATCCAtaattctaga-3'). The modified cry9Aa2 gene was excised as an EcoRI-XbaI fragment (SEQ ID NO: 2) and cloned in a plasmid pPRV312L derivative, which carried the 3'UTR of the rbcL gene (TrbcL; XbaI-HindIII fragment) to yield transformation vector pSKC84. Plastid vector pSKC85 is similar to pSKC84, except that it has a C-terminal c-myc tag (amino acids 410-419; EQKLISEEDL; SEQ ID NO: 4) (Kolodziej & Young, 1991) introduced in a BamHI-XbaI fragment (5'-GGATCCgaacaaaaactcatttctgaa-gaagacttgtgattctaga-3'; SEQ ID NO: 5) with the stop codon. The DNA sequence of the EcoR1-Xba1 fragment in plasmid pSKC85 is SEQ ID NO: 3.

Plastid Transformation

DNA for plastid transformation was prepared using the QIAGEN Plasmid Maxi Kit (QIAGEN Inc., Valencia, Calif.). Transforming DNA was introduced into leaf chloroplasts on the surface of tungsten particles (1 μm) using the Du Pont PDS1000He Biolistic gun (Svab & Maliga, 1993). Transplastomic plants were selected on RMOP medium containing 500 mg/L spectinomycin dihydrochloride. The transgenic plants were grown on MS (Murashige-Skoog) medium (Murashige & Skoog, 1962) containing 3% (w/v) sucrose and 0.6% (w/v) agar in sterile culture condition. A uniform population of transformed plastid genome copies was confirmed by DNA gel blot analysis after digestion with the BstEII restriction enzyme. Double-stranded DNA probes were prepared by random-primed $^{32}$P-labeling using the Ready-To-Go DNA Labeling Beads (Amershem Pharmacia Biotech, Piscataway, N.J.). The probe was the trnI-trnA plastid targeting region, encoded in an EcoRI-HindIII ptDNA fragment.

RNA Gel Blot Analysis

For RNA gel blot analysis (Silhavy & Maliga, 1998) 5 µg total cellular RNA was loaded per lane. Probes were prepared by random-primed $^{32}$P-labeling (see above). The cry9Aa2 and aadA probes were prepared using SwaI and NcoI-XbaI coding region fragments, respectively.

SDS-PAGE and Immunoblotting

Leaves for protein extraction were taken from greenhouse plants. To obtain total soluble leaf protein, about 200 mg leaf was homogenized in 0.1 ml buffer containing 50 mM Hepes/KOH (pH 7.5), 10 mM potassium acetate, 5 mM magnesium acetate, 1 mM EDTA, 10 mM DTT and 2 mM PMSF. Insoluble material from the soluble fraction was removed by centrifugation. The insoluble material was solubilized by adding 0.1 ml solubilization buffer containing 50 mM Hepes/KOH (pH 7.5), 2% lithium dodecyl sulfate and heating for 10 minutes at 95° C. The insoluble material was then removed by centrifugation. Soluble protein concentrations were determined by the Bradford Protein Assay Reagent kit (Bio-Rad, Hercules, Calif.); membrane proteins were quantified with the bicinchoninic acid (BCA) method (Pierce, Rockford, Ill.). The protein in the Comassie Blue stained soluble extracts was quantified with Alpha Innotech (San Leandro, Calif.) Alphaimager IS-2200 using the 1D-Multi Lane densitometry. Immunoblot analysis of Cry9Aa2 accumulation was carried out as described (Carrer et al., 1993) using commercial c-Myc antibody purchased from Santa Cruz Biotechnology, Inc. (Santa Cruz, Calif.).

Insect Bioassay

First, a homogenous, laboratory population of the potato tuber moth was established (Raman & Palacios, 1982). For the detached leaf bioassay fully expanded, young leaves were excised with a sharp blade and placed singly in sterile tissue culture plate on a moist filter paper disk. Five neonate larvae were released on each leaf. Following their incubation at 26° C. for 5 days, the leaf damage and feeding area was recorded. Five leaves were used for each transplastomic line and the experiment was repeated twice.

Results

Construction of Transplastomic Tobacco Plants with Cry9Aa2 Genes

The engineered cry9Aa2 gene was introduced into the plastid genome in the pPRV312L plastid vector, which targets insertions in the trnI-trnA intergenic region located between the rrn16 and rrn23 genes in the plastid rRNA operon. The pPRV312L vector carries a selectable spectinomcyin resistance (aadA) gene flanked by lox-sites for marker gene excision, and a multiple cloning site for passenger genes (FIG. 1A). For expression in plastids, 48 nucleotides of the cry9Aa2 leader and a DNA segment encoding 734 N-terminal amino acids (82.1 kDa) was linked to the 3'-untranslated region of the plastid rbcL gene (TrbcL) and cloned upstream of the selective marker (aadA) (FIG. 1A). The promoter-less cry9Aa2 construct in this vector relies on readthrough transcription from the plastid rRNA operon promoter. Plastid transformation vector pSKC84 encodes the Cry9Aa2 peptide. In vector pSKC85 the Cry9Aa2 C-terminus was fused with a c-myc tag to enable detection by the commercial c-myc antibody. Transplastomic plants were obtained by bombardment of 20 leaves with plasmids pSKC84 and pSKC85, which yielded 26 and 21 spectinomycin resistant clones; of these plastid transformation was confirmed in 13 and 12 clones, respectively. Uniform transformation of plastid genomes was verified by DNA gel blot analysis (FIG. 1B). Plants derived from an independent transformation event are designated by a serial number; letters distinguish plants regenerated from the same clonal event; multiple letters indicate successive cycles of plant regeneration.

Expression of cry9Aa2 Genes in Chloroplasts

RNA gel blot analysis was carried out to test cry9Aa2 mRNA accumulation. The cry9Aa2 transgene is transcribed from the rrn operon promoter (Prrn). Probing of the RNA blot with the cry9Aa2 coding segment revealed mRNAs 2.4- and 2.5-kb in size (FIG. 2). We have observed accumulation of two mRNA species differing with 0.1-kb in size when TrbcL was combined with a loxP site, which forms a 13-nt stem-loop structure (Tungsuchat et al., 2006). Therefore, we assume that the 5'-end of the transcript was generated by maturation of trnI and the 3'-end by processing within the TrbcL or at the loxP-site. In RNA samples from young leaves additional, partially processed mRNA species are visible, which are processing intermediates of the rrn operon transcript (FIG. 1A). Degradation of cry9Aa2 mRNA is apparent in each of the samples.

The selective marker aadA is transcribed from two promoters: its own promoter (PrrnLatpB+DS) and the native rrn operon promoter upstream of rrn16. Probing with aadA revealed two ~1.1-kb monocistronic messages, which did not separate on the blot shown in FIG. 2. These transcripts derive from the aadA gene promoter and from processing of the rrn operon readthrough transcript.

We tested protein accumulation by separating leaf protein extracts in SDS-PAGE. Staining with Comassie Blue revealed a novel band, ~82 kDa in size (FIG. 3A). The novel protein was present in both soluble and membrane protein fractions of transgenic plants. Antibody to the c-myc tag in Nt-pSKC85 plants confirmed the identity of the novel band as a Cry9Aa2 insecticidal protein. The protein in the Comassie Blue stained soluble extracts was quantified with Alpha Innotech Alphaimager IS-2200 using the 1D-Multi Lane densitometry. The Nt-pSKC84 and Nt-pSKC85 leaves contained comparable amounts of Bt protein, ~10% of total soluble protein (FIG. 3A). Immunoblot analysis showed that the Cry9Aa2 protein concentration in the membrane fraction was higher, ~20% (FIG. 3B).

Potato Tuber Moth Bioassay on Tobacco Leaves

Figure 4:
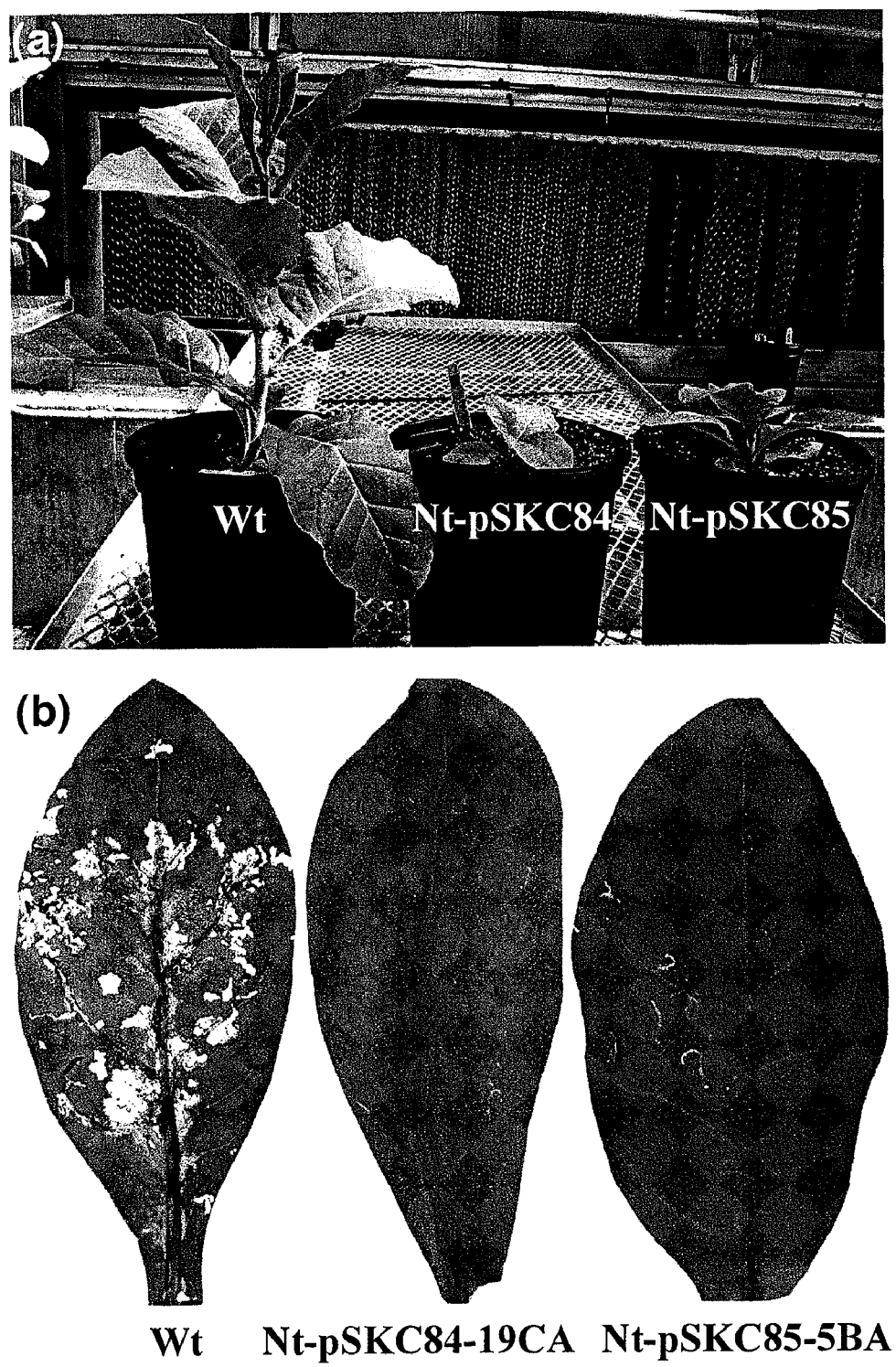

Transgenic plants have been transferred to the greenhouse where they flowered and produced seed. When grown from seed, development of the Nt-pSKC84 and Nt-pSKC85 transgenic plants was significantly delayed and the young leaves had a pale green color (FIG. 4A). However, the older leaves were normal green and plants eventually reached maturity, at which stage they were indistinguishable from wild-type plants. Out of the 12 and 13 independently transformed clones (see above) plants from four lines were studied in greater detail in the greenhouse: Nt-pSKC84-19CA, Nt-pSKC84-16DA and Nt-pSKC85-5BA and Nt-pSKC85-6BB. Seed progeny of each of the lines behaved similarly. Since several, independently transformed lines have the same phenotype, we believe, that the delay in plant development is due to high levels of Cry9aA2 protein accumulations. Furthermore, based on experience with tobacco plants regenerated from hundreds of independently derived transplastomic lines (Bock & Khan, 2004; Maliga, 2004) we are very certain that the delay in plant development is not caused by the transformation method.

Detached leaves of Nt-pSKC84 and Nt-pSKC85 tobacco plants expressing the cry9Aa2 gene have been tested for insecticidal activity against neonate potato tuber moth larvae (FIG. 4B). Transplastomic lines gave complete control of leaf mining by potato tuber moth larvae: 100% larval mortality was observed within 48-72 hrs, whereas no mortality was seen on the control plants for at least 120 hours.

Discussion

The pPRV312L Plastid Vector

The new vector pPRV312L has a multiple cloning site and loxP-flanked (L) aadA marker gene for excision by the CRE recombinase (Corneille et al., 2001; Hajdukiewicz et al., 2001; Lutz et al., 2006). Vector pPRV312L shares the feature of an excisable marker gene with vector pPRV110L (GenBank Accession No. DQ211347) that targets insertions in the trnV-rps12 intergenic region (Lutz et al., 2006). Vector pPRV312L in this study targets insertions between the trnI/trnA genes in the plastid rrn operon. The trnI/trnA intergenic region has been used for insertion of heterologous genes; reviewed in (Daniell et al., 2005). Genes of interest inserted at this site thus far always had their own promoter. Significant levels of protein expression have been obtained only from the rRNA operon (rrn) promoter and the promoter of the psbA gene (Maliga, 2003; Daniell et al., 2005). Expression of multiple genes from polycistronic mRNAs is a more desirable approach, reducing the requirement for promoters. We have shown already that transcriptional fusion with the rbcL mRNA yields significant levels of protein expression (Staub & Maliga, 1995). Expression of the gene of interest in our vector pPRV312L relies on readthrough transcription from the strong rrn operon promoter. High-level accumulation of Cry9Aa2 indicates that transcription from an upstream promoter and translation from a processed 5'-UTR is sufficient for protein expression. In plastids, posttranscriptional gene regulation is important and high-level protein accumulation is dependent on the choice of 5'-UTR (Kuroda & Maliga, 2001 a; Kuroda & Maliga, 2001b); for review see (Maliga, 2003). Thus, the 49 nucleotide B.t. cry9Aa2 5'-UTR is a leader that promotes high-level protein expression in chloroplasts. The 49 Bt nucleotide sequence is: 5'-AACCCAAATAATGTTT-TAAAATTTTAAAAATAA TGTAGGAGGAAAAATT-3'; (SEQ ID NO: 6). DNA sequences encoding the processed 5' UTR and translation initiation codon (ATG), including trnI-trnA intron sequences and the polycloning site, are provided in SEQ ID NO: 4. The B.t. cry2Aa2 leader also promotes high-level protein expression (De Cosa et al., 2001). The 49-nucleotide cry9Aa2 leader sequence reported here is unrelated to the cry2Aa2 leader and lacks the upstream open reading frames, which are present in the cry2Aa2 operon construct.

We used here a 49 nucleotide segment of the native cry9Aa2 5'-UTR, which also promotes high levels of translation. However, mRNA degradation is also apparent on the RNA gel blot. This may be caused by cry9aA2 sequences, which target mRNAs for degradation.

Although the native rrn operon transcript is large (includes rrn16, trnI, trnA, rrn23, rrn4.5, rrn5 genes)(Strittmatter & Kossel, 1984), the large precursor is efficiently processed (Kishine et al., 2004), creating the 5'-UTR of cry9aA2 mRNA. Normally, transcription termination and/or processing of mRNAs within the TrbcL segment used here is inefficient, yielding significant amounts of dicistronic transcripts due to TrbcL readthrough (Serino & Maliga, 1997; Kuroda & Maliga, 2001a; Tregoning et al., 2003). Interestingly, in this case dicistronic ~3.5-kb cry9aA2-aadA mRNAs were absent in mature leaves, suggesting efficient transcription termination and/or mRNA processing due to having loxP downstream of TrbcL (Tungsuchat et al., 2006).

Insect Biocontrol with Plastid-Expressed Cry9Aa2

Because of its strong insecticidal activity against larvae (LC50=80 ng per ml diet for 5 days), Cry9Aa2 Bt insecticidal protein is highly desirable for the biocontrol of potato tuber moth (Gleave et al., 1998). Lethality from a codon-modified nuclear gene yielded at least 75% larval mortality in nine days. Larval mortality caused by expression of Cry9Aa2 in plastids in our study was significantly higher, 100% within two-to-three days.

High-level expression (10% of soluble, 20% of membrane protein) of Cry9Aa2 protein came at a price of significantly delayed plant development. In earlier publications, plastid-expressed Bt insecticidal proteins also accumulated to relatively high levels in leaves: 5% cry1Ac (McBride et al., 1995), 3% (Kota et al., 1999) and 45.3% (De Cosa et al., 2001) cry2Aa2 and 3% cry1Ia5 (Reddy et al., 2002). Interestingly, no adverse affect of B.t. protein expression was reported on plant development in any of these studies. 100% larval mortality was observed even if the B.t. proteins were expressed at relatively modest (3%-5%) levels (McBride et al., 1995; Kota et al., 1999; Reddy et al., 2002). Thus, expression of Cry9Aa2 at significantly lower levels should be sufficient to achieve efficient insecticidal control. To create a useful cry9aA2 construct one is facing the unusual task of down-regulating translation efficiency.

REFERENCES

Beuning L L, Mitra D S, Marwick N P and Gleave A P. (2001) Minor modifications to the cry1Ac9 nucleotide sequence are sufficient to generate transgenic plants resistant to *Phthorimaea operculella*. Ann Appl Biol, 138, 281-292.

Bock R and Khan M R. (2004) Taming plastids for a green future. Trends Biotech, 22, 311-318.

Carrer H, Hockenberry T N, Svab Z and Maliga P. (1993) Kanamycin resistance as a selectable marker for plastid transformation in tobacco. Mol Gen Genet, 241, 49-56.

Chan M T, Chen L J and Chang H H. (1996) Expression of *Bacillus thuringiensis* (B.t.) insecticidal crystal protein gene in transgenic potato. Bot Bull Acad Sinica, 37, 17-23.

Corneille S, Lutz K, Svab Z and Maliga P. (2001) Efficient elimination of selectable marker genes from the plastid genome by the CRE-lox site-specific recombination system. Plant J, 72, 171-178.

Crickmore N, Zeigler D R, Feitelson J, Schnepf E, Van Rie J, Lereclus D, Baum J and Dean D H. (1998) Revision of the nomenclature for the *Bacillus thuringiensis* pesticidal crystal protein. Microbio Mol Biol Rev, 62, 807-813.

Daniell H, Kumar S and Dufourmantel N. (2005) Breakthrough in chloroplast genetic engineering of agronomically important crops. Trends Biotech, 23, 238-245.

Davidson M M, Jacobs J M E, Reader J K, Butler R C, Frater C M, Markwick N P, Wratten S D and Conner A J. (2002) Development and evolution of potatoes transgenic for a cry1Ac9 gene conferring resistance to potato tuber moth. J Amer Soc Hort Sci, 127, 590-596.

De Cosa B, Moar W, Lee S B, Miller M and Daniell H. (2001) Overexpression of the Bt cry2Aa2 operon in chloroplasts leads to formation of insecticidal crystals. Nat Biotechnol, 19, 71-74.

Douches D S, Li W, Zarka K, Coombs J, Pett W, Grafius E and El-Nasr T. (2002) Development of Bt-cry5 insect-resistant potato lines 'Spunta-G2' and 'Spunta-G3'. *HortScience*, 37, 1103-1107.

Ebora R V, Ebora M M and Sticklen M B. (1994) Transgenic potato expressing the *Bacillus thuringiensis* cry1A(c) gene effects the survival and food consumption of *Phthorimea operculella* (Lepidoptera: Gelechiidae) and *Ostrania nubilalis* (Lepidoptera: Noctuidae). *J Econ Entomol*, 87, 1122-1127.

Gleave A P, Hedges R J and Broadwell A H. (1992) Identification of an insecticidal crystal protein from *Bacillus thuringiensis* DSIR517 with significant sequence differences from previously described toxins. *J Gen Microbiol*, 138, 55-62.

Gleave A P, Mitra D S, Markwick N P, Morris B A M and Beuining L L. (1998) Enhanced expression of the *Bacillus thuringiensis* cry9Aa2 gene in transgenic plants by nucleotide sequence modification confers resistance to potato tuber moth. *Mol Breeding*, 4, 459-472.

Hajdukiewicz P T J, Gilbertson L and Staub J M. (2001) Multiple pathways for Cre/lox-mediated recombination in plastids. *Plant J*, 27, 161-170.

Jansens S, Cornelissen M, de Clercq R, Reynaerts A and Peferoen M. (1995) *Phthorimea operculella* (Lepidoptera: Gelechiidae) resistance in potato by expression of the *Bacillus thuringiensis* Cry1A(b) insecticidal crystal protein. *J Econ Entomol*, 88, 1469-1476.

Kishine M, Takabayashi A, Munekage Y, Shikanai T, Endo T and Sato F. (2004) Ribosomal RNA processing and an RNase R family member in chloroplasts of *Arabidopsis*. *Plant Mol Biol*, 55, 595-606.

Kolodziej P A and Young R A. (1991) Epitope tagging and protein surveillance. *Methods Enzymol*, 194, 508-519.

Kota M, Daniell H, Varma S, Garczynski S F, Gould F and Moar W J. (1999) Overexpression of the *Bacillus thuringiensis* (Bt) Cry2Aa2 protein in chloroplasts confers resistance to plants against susceptible and Bt-resistant insects. *Proc Natl Acad Sci USA*, 96, 1840-1845.

Kuroda H and Maliga P. (2001a) Sequences downstream of the translation initiation codon are important determinants of translation efficiency in chloroplasts. *Plant Physiol*, 125, 430-436.

Kuroda H and Maliga P. (2001b) Complementarity of the 16S rRNA penultimate stem with sequences downstream of the AUG destabilizes the plastid mRNAs. *Nucleic Acids Res*, 29, 970-975.

Lutz K A, Bosacchi M H and Maliga P. (2006) Plastid marker gene excision by transiently expressed CRE recombinase. *Plant J*, 45, 447-456.

Maliga P. (2003) Progress towards commercialization of plastid transformation technology. *Trends Biotech*, 21, 20-28.

Maliga P. (2004) Plastid transformation in higher plants. *Annu Rev Plant Biol*, 55, 289-313.

McBride K E, Svab Z, Schaaf D J, Hogan P S, Stalker D M and Maliga P. (1995) Amplification of a chimeric *Bacillus* gene in chloroplasts leads to an extraordinary level of an insecticidal protein in tobacco. *Biotechnology*, 13, 362-365.

Mohammed A, Douches D S, Pett W, Grafius E, Coombs J, Liswidowati, Li W and Madkour M A. (2000) Evaluation of potato tuber moth (Lepidoptera: Gelechiidae) resistance in tubers of Bt-cry5 transgenic potato lines. *J Econ Entomol*, 93, 472-476.

Murashige T and Skoog F. (1962) A revised medium for the growth and bioassay with tobacco tissue culture. *Physiol Plant*, 15, 473-497.

Murray E E, Rocheleau T, Eberle M, Stock C, Sekar V and Adang M. (1991) Analysis of unstable RNA transcripts of insecticidal crystal protein genes of *Bacillus thuringiensis* in transgenic plants and electroporated protoplasts. *Plant Mol Biol*, 16, 1035-1050.

Naimov S, Dukiandjiev S, Ruud A and de Maagd R A. (2003) A hybrid *Bacillus thuringiensis* delta-endotoxin gives resistance against a coleopteran and a lepidopteran pest in transgenic potato. *Plant Biotechnol J*, 1, 51-57.

Raman K V and Palacios M. (1982) Screening potato for resistance to potato tuberworm. man, K. V. *J Econ Entomol*, 75, 47-49.

Reddy V S, Leelavathi S, Selvapandiyan A, Raman R, Giovanni F, Shukla V and Bhatnagar R K. (2002) Analysis of chloroplast transformed tobacco plants with cry1Ia5 under rice psbA transcriptional elements reveal high level expression of Bt toxin without imposing yield penalty and stable inheritance of transplastome. *Mol Breeding*, 9, 259-269.

Serino G and Maliga P. (1997) A negative selection scheme based on the expression of cytosine deaminase in plastids. *Plant J*, 12, 697-701.

Shinozaki K, Ohme M, Tanaka M, Wakasugi T, Hayashida N, Matsubayashi T, Zaita N, Chunwongse J, Obokata J, Yamaguchi-Shinozaki K, Ohto C, Torazawa K, Meng B-Y, Sugita M, Deno H, Kamogashira T, Yamada K, Kusuda J, Takaiwa F, Kato A, Tohdoh N, Shimada H and Sugiura M. (1986) The complete nucleotide sequence of the tobacco chloroplast genome: its gene organization and expression. *EMBO J*, 5, 2043-2049.

Silhavy D and Maliga P. (1998) Mapping of the promoters for the nucleus-encoded plastid RNA polymerase (NEP) in the iojap maize mutant. *Curr Genet*, 33, 340-344.

Staub J M and Maliga P. (1995) Expression of a chimeric uidA gene indicates that polycistronic mRNAs are efficiently translated in tobacco plastids. *Plant J*, 7, 845-848.

Strittmatter G and Kossel H. (1984) Cotranscription and processing of 23S, 4.5S and 5S rRNA in chloroplasts from *Zea mays*. *Nucleic Acids Res*, 12, 7633-7647.

Svab Z and Maliga P. (1993) High-frequency plastid transformation in tobacco by selection for a chimeric aadA gene. *Proc Natl Acad Sci USA*, 90, 913-917.

Tregoning J, Nixon P, Kuroda H, Svab Z, Clare S, Bowe F, Fairweather N, Ytterberg J, van Wijk K J, Dougan G and Maliga P. (2003) Expression of tetanus toxin fragment C in tobacco chloroplasts. *Nucleic Acids Res*, 31, 1174-1179.

Tungsuchat T, Kuroda H, Narangajavana J and Maliga P. (2006) Gene activation in plastids by the CRE site-specific recombinase. *Plant Mol Biol*, 61:711-718.

APPENDIX A

Sequence Information

SEQ ID NO: 1
DNA sequence of plastid transformation pPRV312L;
vector with floxed aadA in trnI/trnA intergenic
region; in pUC118 vector derivative (circular DNA)
pPRV312L.seq; GenBank DQ489715 Length: 6348
GGGCCTTGTA CACACCGCCC GTCACACTAT GGGAGCTGGC

CATGCCCGAA GTCGTTACCT TAACCGCAAG GAGGGGGATG

CCGAAGGCAG GGCTAGTGAC TGGAGTGAAG TCGTAACAAG

GTAGCCGTAC TGGAAGGTGC GGCTGGATCA CCTCCTTTTC

APPENDIX A-continued

Sequence Information

AGGGAGAGCT AATGCTTGTT GGGTATTTTG GTTTGACACT
GCTTCACACC CCCAAAAAAA AGAAGGGAGC TACGTCTGAG
TTAAACTTGG AGATGGAAGT CTTCTTTCCT TTCTCGACGG
TGAAGTAAGA CCAAGCTCAT GAGCTTATTA TCCTAGGTCG
GAACAAGTTG ATAGGACCCC CTTTTTTACG TCCCCATGTT
CCCCCCGTGT GGCGACATGG GGGCGAAAAA AGGAAAGAGA
GGGATGGGGT TTCTCTCGCT TTTGGCATAG CGGGCCCCCA
GTGGGAGGCT CGCACGACGG GCTATTAGCT CAGTGGTAGA
GCGCGCCCCT GATAATTGCG TCGTTGTGCC TGGGCTGTGA
GGGCTCTCAG CCACATGGAT AGTTCAATGT GCTCATCGGC
GCCTGACCCT GAGATGTGGA TCATCCAAGG CACATTAGCA
TGGCGTACTC CTCCTGTTCG AACCGGGGTT TGAAACCAAA
CTCCTCCTCA GGAGGATAGA TGGGGCGATT CGGGTGAGAT
CCAATGTAGA TCCAACTTTC GATTCACTCG TGGGATCCGG
GCGGTCCGGG GGGGACCACC ACGGCTCCTC TCTTCTCGAG
AATCCATACA TCCCTTATCA GTGTATGGAC AGCTATCTCT
CGAGCACAGG TTTAGCAATG GGAAAATAAA ATGGAGCACC
TAACAACGCA TCTTCACAGA CCAAGAACTA CGAGATCGCC
CCTTTCATTC TGGGGTGACG GAGGGATCGT ACCATTCGAG
CCGTTTTTTT CTTGACTCGA AATGGGAGCA GGTTTGAAAA
AGGATCTTAG AGTGTCTAGG GTTGGGCCAG GAGGGTCTCT
TAACGCCTTC TTTTTTCTTC TCATCGGAGT TATTTCACAA
AGACTTGCCA GGGTAAGGAA GAAGGGGGGA ACAAGCACAC
TTGGAGAGCG CAGTACAACG GAGAGTTGTA TGCTGCGTTC
GGGAAGGATG AATCGCTCCC GAAAAGGAAT CTATTGATTC
TCTCCCAATT GGTTGGACCG TAGGTGCGAT GATTTACTTC
ACGGGCGAGG TCTCTGGTTC AAGTCCAGGA TGGCCCAGCT
GCATTTAAAT GGCGCGCCGA ATTCGAGCTC GGTACCCGGG
GATCCTCTAG AGTCGACCTG CAGGCATGCA AGCTTGCGGC
CGCagtAGCT TATAACTTCG TATAGCATAC ATTATACGAA
GTTATagatc cGCTCCCCCG CCGTCGTTCA ATGAGAATGG
ATAAGAGGC CGTGGGATTG ACGTGAGGGG CAGGGATGG
CTATATTTCT GGGAGAATTA ACCGATCGAC GTGCaAGCGG
ACATTTATTT TaAATTCGAT AATTTTTGCA AAAACATTTC
GACATATTTA TTTATTTTAT TATTATGAGA ATCAATCCTA
CTACTTCTGG TTCTGGGGTT TCCACGgcta gtagcGAAGC
GGTGATCGCC GAAGTATCGA CTCAACTATC AGAGGTAGTT
GGCGTCATCG AGCGCCATCT CGAACCGACG TTGCTGGCCG
TACATTTGTA CGGCTCCGCA GTGGATGGCG GCCTGAAGCC ACACAGTGAT ATTGATTTGC TGGTTACGGT GACCGTAAGG
CTTGATGAAA CAACGCGGCG AGCTTTGATC AACGACCTTT
TGGAAACTTC GGCTTCCCCT GGAGAGAGCG AGATTCTCCG
CGCTGTAGAA GTCACCATTG TTGTGCACGA CGACATCATT
CCGTGGCGTT ATCCAGCTAA GCGCGAACTG CAATTTGGAG
AATGGCAGCG CAATGACATT CTTGCAGGTA TCTTCGAGCC
AGCCACGATC GACATTGATC TGGCTATCTT GCTGACAAAA
GCAAGAGAAC ATAGCGTTGC CTTGGTAGGT CCAGCGGCGG
AGGAACTCTT TGATCCGGTT CCTGAACAGG ATCTATTTGA
GGCGCTAAAT GAAACCTTAA CGCTATGGAA CTCGCCGCCC
GACTGGGCTG GCGATGAGCG AAATGTAGTG CTTACGTTGT
CCCGCATTTG GTACAGCGCA GTAACCGGCA AAATCGCGCC
GAAGGATGTC GCTGCCGACT GGGCAATGGA GCGCCTGCCG
GCCCAGTATC AGCCCGTCAT ACTTGAAGCT AGACAGGCTT
ATCTTGGACA AGAAGAAGAT CGCTTGGCCT CGCGCGCAGA
TCAGTTGGAA GAATTTGTCC ACTACGTGAA AGGCGAGATC
ACCAAGGTAG TgGGCAAAga acaaaaactc atttctgaag
aagacttgtg agtctagcta gaGCGATCCT GGCCTAGTCT
ATAGGAGGTT TTGAAAAGAA AGGAGCAATA ATCATTTTCT
TGTTCTATCA AGAGGGTGCT ATTGCTCCTT TCTTTTTTC
TTTTTATTTA TTTACTAGTA TTTTACTTAC ATAGACTTTT
TTGTTTACAT TATAGAAAAA GAAGGAGAGG TTATTTTCTT
GCATTTATTC ATGggggatc aaagctgatc tATAACTTCG
TATAGCATAC ATTATACGAA GTTATggtac actATTTAAA
TgcgCTCCAC TTGGCTCGGG GGGATATAGC TCAGTTGGTA
GAGCTCCGCT CTTGCAATTG GGTCGTTGCG ATTACGGGTT
GGATGTCTAA TTGTCCAGGC GGTAATGATA GTATCTTGTA
CCTGAACCGG TGGCTCACTT TTTCTAAGTA ATGGGGAAGA
GGACCGAAAC GTGCCACTGA AGACTCTAC TGAGACAAAG
ATGGGCTGTC AAGAACGTAG AGGAGGTAGG ATGGGCAGTT
GGTCAGATCT AGTATGGATC GTACATGGAC GGTAGTTGGA
GTCGGCGGCT CTCCCAGGGT TCCCTCATCT GAGATCTCTG
GGGAAGAGGA TCAAGTTGGC CCTTGCGAAC AGCTTGATGC
ACTATCTCCC TTCAACCCTT TGAGCGAAAT GCGGCAAAAG
AAAAGGAAGG AAAATCCATG GACCGACCCC ATCATCTCCA
CCCCGTAGGA ACTACGAGAT CACCCCAAGG ACGCCTTCGG
CATCCAGGGG TCACGGACCG ACCATAGAAC CCTGTTCAAT
AAGTGGAACG CATTAGCTGT CCGCTCTCAG GTTGGGCAGT
CAGGGTCGGA GAAGGGCAAT GACTCATTCT TAGTTAGAAT

APPENDIX A-continued

Sequence Information

GGGATTCCAA CTCAGCACCT TTTGAGTGAG ATTTTGAGAA
GAGTTGCTCT TTGGAGAGCA CAGTACGATG AAAGTTGTAA
GCTGTGTTCG GGGGGGAGTT ATTGTCTATC GTTGGCCTCT
ATGGTAGAAT CAGTCGGGGG ACCTGAGAGG CGGTGGTTTA
CCCTGCGGCG GATGTCAGCG GTTCGAGTCC GCTTATCTCC
AACTCGTGAA CTTAGCCGAT ACAAAGCTCT GGCGTAATAG
CGAAGAGGCC CGCACCGATC GCCCTTCCCA ACAGTTGCGC
AGCCTGAATG GCGAATGGCG CCTGATGCGG TATTTTCTCC
TTACGCATCT GTGCGGTATT TCACACCGCA TACGTCAAAG
CAACCATAGT ACGCGCCCTG TAGCGGCGCA TTAAGCGCGG
CGGGTGTGGT GGTTACGCGC AGCGTGACCG CTACACTTGC
CAGCGCCCTA GCGCCCGCTC CTTTCGCTTT CTTCCCTTCC
TTTCTCGCCA CGTTCGCCGG CTTTCCCCGT CAAGCTCTAA
ATCCGGGGCT CCCTTTAGGG TTCCGATTTA GTGCTTTACG
GCACCTCGAC CCCAAAAAAC TTGATTTGGG TGATGGTTCA
CGTAGTGGGC CATCGCCCTG ATAGACGGTT TTTCGCCCTT
TGACGTTGGA GTCCACGTTC TTTAATAGTG GACTCTTGTT
CCAAACTGGA ACAACACTCA ACCCTATCTC GGGCTATTCT
TTTGATTTAT AAGGGATTTT GCCGATTTCG GCCTATTGGT
TAAAAAATGA GCTGATTTAA CAAAAATTTA ACGCGAATTT
TAACAAAATA TTAACGTTTA CAATTTTATG GTGCACTCTC
AGTACAATCT GCTCTGATGC CGCATAGTTA AGCCAGCCCC
GACACCCGCC AACACCCGCT GACGCGCCCT GACGGGCTTG
TCTGCTCCCG GCATCCGCTT ACAGACAAGC TGTGACCGTC
TCCGGGAGCT GCATGTGTCA GAGGTTTTCA CCGTCATCAC
CGAAACGCGC GAGACGAAAG GGCCTCGTGA TACGCCTATT
TTTATAGGTT AATGTCATGA TAATAATGGT TTCTTAGACG
TCAGGTGGCA CTTTTCGGGG AAATGTGCGC GGAACCCCTA
TTTGTTTATT TTTCTAAATA CATTCAAATA TGTATCCGCT
CATGAGACAA TAACCCTGAT AAATGCTTCA ATAATATTGA
AAAAGGAAGA GTATGAGTAT TCAACATTTC CGTGTCGCCC
TTATTCCCTT TTTTGCGGCA TTTTGCCTTC CTGTTTTTGC
TCACCCAGAA ACGCTGGTGA AAGTAAAAGA TGCTGAAGAT
CAGTTGGGTG CACGAGTGGG TTACATCGAA CTGGATCTCA
ACAGCGGTAA GATCCTTGAG AGTTTTCGCC CCGAAGAACG
TTTTCCAATG ATGAGCACTT TTAAAGTTCT GCTATGTGGC
GCGGTATTAT CCCGTATTGA CGCCGGGCAA GAGCAACTCG
GTCGCCGCAT ACACTATTCT CAGAATGACT TGGTTGAGTA
TTCACCAGTC ACAGAAAAGC ATCTTACGGA TGGCATGACA

GTAAGAGAAT TATGCAGTGC TGCCATAACC ATGAGTGATA
ACACTGCGGC CAACTTACTT CTGACAACGA TCGGAGGACC
GAAGGAGCTA ACCGCTTTTT TGCACAACAT GGGGGATCAT
GTAACTCGCC TTGATCGTTG GGAACCGGAG CTGAATGAAG
CCATACCAAA CGACGAGCGT GACACCACGA TGCCTGTAGC
AATGGCAACA ACGTTGCGCA ACTATTAAC TGGCGAACTA
CTTACTCTAG CTTCCCGGCA CAATTAATA GACTGGATGG
AGGCGGATAA AGTTGCAGGA CCACTTCTGC GCTCGGCCCT
TCCGGCTGGC TGGTTTATTG CTGATAAATC TGGAGCCGGT
GAGCGTGGGT CTCGCGGTAT CATTGCAGCA CTGGGGCCAG
ATGGTAAGCC CTCCCGTATC GTAGTTATCT ACACGACGGG
GAGTCAGGCA ACTATGGATG AACGAAATAG ACAGATCGCT
GAGATAGGTG CCTCACTGAT TAAGCATTGG TAACTGTCAG
ACCAAGTTTA CTCATATATA CTTTAGATTG ATTTAAAACT
TCATTTTTAA TTTAAAAGGA TCTAGGTGAA GATCCTTTTT
GATAATCTCA TGACCAAAAT CCCTTAACGT GAGTTTTCGT
TCCACTGAGC GTCAGACCCC GTAGAAAAGA TCAAAGGATC
TTCTTGAGAT CCTTTTTTTC TGCGCGTAAT CTGCTGCTTG
CAAACAAAAA AACCACCGCT ACCAGCGGTG GTTTGTTTGC
CGGATCAAGA GCTACCAACT CTTTTTCCGA AGGTAACTGG
CTTCAGCAGA GCGCAGATAC CAAATACTGT CCTTCTAGTG
TAGCCGTAGT TAGGCCACCA CTTCAAGAAC TCTGTAGCAC
CGCCTACATA CCTCGCTCTG CTAATCCTGT TACCAGTGGC
TGCTGCCAGT GGCGATAAGT CGTGTCTTAC CGGGTTGGAC
TCAAGACGAT AGTTACCGGA TAAGGCGCAG CGGTCGGGCT
GAACGGGGGG TTCGTGCACA CAGCCCAGCT TGGAGCGAAC
GACCTACACC GAACTGAGAT ACCTACAGCG TGAGCTATGA
GAAAGCGCCA CGCTTCCCGA AGGGAGAAAG CGGACAGGT
ATCCGGTAAG CGGCAGGGTC GGAACAGGAG AGCGCACGAG
GGAGCTTCCA GGGGGAAACG CCTGGTATCT TTATAGTCCT
GTCGGGTTTC GCCACCTCTG ACTTGAGCGT CGATTTTTGT
GATGCTCGTC AGGGGGGCGG AGCCTATGGA AAAACGCCAG
CAACGCGGCC TTTTTACGGT TCCTGGCCTT TGCTGGCCT
TTTGCTCACA TGTTCTTTCC TGCGTTATCC CCTGATTCTG
TGGATAACCG TATTACCGCC TTTGAGTGAG CTGATACCGC
TCGCCGCAGC CGAACGACCG AGCGCAGCGA GTCAGTGAGC
GAGGAAGCGG AAGAGCGCCC AATACGCAAA CCGCCTCTCC
CCGCGCGTTG GCCGATTCAT TAATGCAG.

APPENDIX A-continued

Sequence Information

SEQ ID NO: 2
EcoRI-XbaI fragment in plasmid cry9Aa2pSKC84.seq
2277 nucleotides
   gaattccg tcgaggtcAA CCCAAATAAT GTTTTAAAAT
TTTAAAAATA ATGTAGGAGG AAAAATTATG AATCAAAATA
AACACGGAAT TATTGGCGCT TCCAATTGTG GTTGTGCATC
TGATGATGTT GCGAAATATC CTTTAGCCAA CAATCCATAT
TCATCTGCTT TAAATTTAAA TTCTTGTCAA AATAGTAGTA
TTCTCAACTG GATTAACATA ATAGGCGATG CAGCAAAAGA
AGCAGTATCT ATTGGGACAA CCATAGTCTC TCTTATCACA
GCACCTTCTC TTACTGGATT AATTTCAATA GTATATGACC
TTATAGGTAA AGTACTAGGA GGTAGTAGTG GACAATCCAT
ATCAGATTTG TCTATATGTG ACTTATTATC TATTATTGAT
TTACGGGTAA GTCAGAGTGT TTTAAATGAT GGGATTGCAG
ATTTTAATGG TTCTGTACTC TTATACAGGA ACTATTTAGA
GGCTCTGGAT AGCTGGAATA AGAATCCTAA TTCTGCTTCT
GCTGAAGAAC TCCGTACTCG TTTTAGAATC GCCGACTCAG
AATTTGATAG AATTTTAACC CGAGGGTCTT AACGAATGG
TGGCTCGTTA GCTAGACAAA ATGCCCAAAT ATTATTATTA
CCTTCTTTTG CGAGCGCTGC ATTTTTCCAT TTATTACTAC
TAAGGGATGC TACTAGATAT GGCACTAATT GGGGGCTATA
CAATGCTACA CCTTTTATAA ATTATCAATC AAAACTAGTA
GAGCTTATTG AACTATATAC TGATTATTGC GTACATTGGT
ATAATCGAGG TTTCAACGAA CTAAGACAAC GAGGCACTAG
TGCTACAGCT TGGTTAGAAT TCATAGATA TCGTAGAGAG
ATGACATTGA TGGTATTAGA TATAGTAGCA TCATTTTCAA
GTCTTGATAT TACTAATTAC CCAATAGAAA CAGATTTTCA
GTTGAGTAGG GTCATTTATA CAGATCCAAT TGGTTTTGTA
CATCGTAGTA GTCTTAGGGG AGAAAGTTGG TTTAGCTTTG
TTAATAGAGC TAATTTCTCA GATTTAGAAA ATGCAATACC
TAATCCTAGA CCGTCTTGGT TTTTAAATAA TATGATTATA
TCTACTGGTT CACTTACATT GCCGGTTAGC CCAAGTACTG
ATAGAGCGAG GGTATGGTAT GGAAGTCGAG ATCGAATTTC
CCCTGCTAAT TCACAATTTA TTACTGAACT AATCTCTGGA
CAACATACGA CTGCTACACA AACTATTTTA GGGCGAAATA
TATTTAGAGT AGATTCTCAA GCTTGTAATT TAAATGATAC
CACATATGGA GTGAATAGGG CGGTATTTTA TCATGATGCG
AGTGAAGGTT CTCAAAGATC CGTGTACGAG GGGTATATTC
GAACAACTGG GATAGATAAC CCTAGAGTTC AAAATATTAA
CACTTATTTA CCTGGAGAAA ATTCAGATAT CCCAACTCCA GAAGACTATA CTCATATATT AAGCACAACA ATAAATTTAA
CAGGAGGACT TAGACAAGTA GCATCTAATC GCCGTTCATC
TTTAGTAATG TATGGTTGGA CACATAAAAG TCTGGCTCGT
AACAATACCA TTAATCCAGA TAGAATTACA CAGATACCAT
TGACGAAGGT TGATACCCGA GGCACAGGTG TTTCTTATGT
GAATGATCCA GGATTTATAG GAGGAGCTCT ACTTCAAAGG
ACTGACCATG GTTCGCTTGG AGTATTGAGG GTCCAATTTC
CACTTCACTT AAGACAACAA TATCGTATTA GAGTCCGTTA
TGCTTCTACA ACAAATATTC GATTGAGTGT GAATGGCAGT
TTCGGTACTA TTTCTCAAAA TCTCCCTAGT ACAATGAGAT
TAGGAGAGGA TTTAAGTAC GGATCTTTTG CTATAAGAGA
GTTTAATACT TCTATTAGAC CCACTGCAAG TCCGGACCAA
ATTCGATTGA CAATAGAACC ATCTTTTATT AGACAAGAGG
TCTATGTAGA TAGAATTGAG TTCATTCCAG TTAATCCGAC
GCGAGAGGCG AAAGAGGATC TAGAAGCAGC AAAAAAAGCG
GTGGCGAGCT TGTTTACACG CACAAGGGAC GGATTACAAG
TAAATGTGAA AGATTATCAA GTCGATCAAG CGGCAAATTT
AGTGTCATGC TTATCAGATG AACAATATGG GTATGACAAA
AAGATGTTAT TGGAAGCGGT ACGTGCGGCA AAACGACTTA
GCCGAGAACG CAACTTACTT CAGGATCCAt aattctaga SEQ ID NO: 3
EcoRI-XbaI fragment in plasid pSKC85, with c-myc
tagged cry9Aa2 gene. 2307 nucleotides
   gaattccg tcgaggtcAA CCCAAATAAT GTTTTAAAAT
TTTAAAAATA ATGTAGGAGG AAAAATTATG AATCAAAATA
AACACGGAAT TATTGGCGCT TCCAATTGTG GTTGTGCATC
TGATGATGTT GCGAAATATC CTTTAGCCAA CAATCCATAT
TCATCTGCTT TAAATTTAAA TTCTTGTCAA AATAGTAGTA
TTCTCAACTG GATTAACATA ATAGGCGATG CAGCAAAAGA
AGCAGTATCT ATTGGGACAA CCATAGTCTC TCTTATCACA
GCACCTTCTC TTACTGGATT AATTTCAATA GTATATGACC
TTATAGGTAA AGTACTAGGA GGTAGTAGTG GACAATCCAT
ATCAGATTTG TCTATATGTG ACTTATTATC TATTATTGAT
TTACGGGTAA GTCAGAGTGT TTTAAATGAT GGGATTGCAG
ATTTTAATGG TTCTGTACTC TTATACAGGA ACTATTTAGA
GGCTCTGGAT AGCTGGAATA AGAATCCTAA TTCTGCTTCT
GCTGAAGAAC TCCGTACTCG TTTTAGAATC GCCGACTCAG
AATTTGATAG AATTTTAACC CGAGGGTCTT AACGAATGG
TGGCTCGTTA GCTAGACAAA ATGCCCAAAT ATTATTATTA
CCTTCTTTTG CGAGCGCTGC ATTTTTCCAT TTATTACTAC
TAAGGGATGC TACTAGATAT GGCACTAATT GGGGGCTATA

APPENDIX A-continued
Sequence Information

```
CAATGCTACA CCTTTTATAA ATTATCAATC AAAACTAGTA
GAGCTTATTG AACTATATAC TGATTATTGC GTACATTGGT
ATAATCGAGG TTTCAACGAA CTAAGACAAC GAGGCACTAG
TGCTACAGCT TGGTTAGAAT TTCATAGATA TCGTAGAGAG
ATGACATTGA TGGTATTAGA TATAGTAGCA TCATTTTCAA
GTCTTGATAT TACTAATTAC CCAATAGAAA CAGATTTTCA
GTTGAGTAGG GTCATTTATA CAGATCCAAT TGGTTTTGTA
CATCGTAGTA GTCTTAGGGG AGAAAGTTGG TTTAGCTTTG
TTAATAGAGC TAATTTCTCA GATTTAGAAA ATGCAATACC
TAATCCTAGA CCGTCTTGGT TTTTAAATAA TATGATTATA
TCTACTGGTT CACTTACATT GCCGGTTAGC CCAAGTACTG
ATAGAGCGAG GGTATGGTAT GGAAGTCGAG ATCGAATTTC
CCCTGCTAAT TCACAATTTA TTACTGAACT AATCTCTGGA
CAACATACGA CTGCTACACA AACTATTTTA GGGCGAAATA
TATTTAGAGT AGATTCTCAA GCTTGTAATT TAAATGATAC
CACATATGGA GTGAATAGGG CGGTATTTTA TCATGATGCG
AGTGAAGGTT CTCAAAGATC CGTGTACGAG GGGTATATTC
GAACAACTGG GATAGATAAC CCTAGAGTTC AAAATATTAA
CACTTATTTA CCTGGAGAAA ATTCAGATAT CCCAACTCCA
GAAGACTATA CTCATATATT AAGCACAACA ATAAATTTAA
CAGGAGGACT TAGACAAGTA GCATCTAATC GCCGTTCATC
TTTAGTAATG TATGGTTGGA CACATAAAAG TCTGGCTCGT
AACAATACCA TTAATCCAGA TAGAATTACA CAGATACCAT
TGACGAAGGT TGATACCCGA GGCACAGGTG TTTCTTATGT
GAATGATCCA GGATTTATAG GAGGAGCTCT ACTTCAAAGG
```

```
ACTGACCATG GTTCGCTTGG AGTATTGAGG GTCCAATTTC
CACTTCACTT AAGACAACAA TATCGTATTA GAGTCCGTTA
TGCTTCTACA ACAAATATTC GATTGAGTGT GAATGGCAGT
TTCGGTACTA TTTCTCAAAA TCTCCCTAGT ACAATGAGAT
TAGGAGAGGA TTTAAGATAC GGATCTTTTG CTATAAGAGA
GTTTAATACT TCTATTAGAC CCACTGCAAG TCCGGACCAA
ATTCGATTGA CAATAGAACC ATCTTTTATT AGACAAGAGG
TCTATGTAGA TAGAATTGAG TTCATTCCAG TTAATCCGAC
GCGAGAGGCG AAAGAGGATC TAGAAGCAGC AAAAAAAGCG
GTGGCGAGCT TGTTTACACG CACAAGGGAC GGATTACAAG
TAAATGTGAA AGATTATCAA GTCGATCAAG CGGCAAATTT
AGTGTCATGC TTATCAGATG AACAATATGG GTATGACAAA
AAGATGTTAT TGGAAGCGGT ACGTGCGGCA AAACGACTTA
GCCGAGAACG CAACTTACTT CAGGATCCAg aacaaaaact
catttctgaa gaagacttgt gattctaga
```

SEQ ID NO: 4
DNA sequence encoding the processed 5'-UTR in plasmids pSKC84 and pSKC85 including the ATG translation initiation codon. The 49 Bt nucleotides upstream of the ATG are in bold.
GCTGcATTTAAATGGCGCGCC gaattccg tcgaggtc AA

CCCAAATAAT GTTTTAAAAT TTTAAAAATA ATGTAGGAGG

AAAAATT ATG

While certain preferred embodiments of the present invention have been described and specifically exemplified above, it is not intended that the invention be limited to such embodiments. Various modifications may be made to the invention without departing from the scope and spirit thereof as set forth in the following claims.

---

What is claimed is:

1. A nucleic acid construct for high levels of translation for increasing heterologous protein production in a plastid of a higher plant, said construct comprising in the 5' to 3' direction,
   a) a 5' nucleic acid sequence comprising a 49 nucleotide segment of the native cry9Aa2 5'-UTR of SEQ ID NO:4;
   b) a nucleic acid sequence encoding at least one heterologous protein or polypeptide of interest; and
   c) a transcription termination region, said construct optionally further comprising a nucleic acid encoding a selectable marker,
   wherein a), b) and c), and said selectable marker encoding nucleic acid, if present, are flanked by homologous nucleic acid sequences obtained from the genome of said plastid, said homologous nucleic acid sequences directing homologous recombination of said construct into said plastid genome, such that said heterologous protein or polypeptide is produced.

2. The construct of claim 1, wherein said heterologous protein is selected from the group consisting of at least one of antibodies, hormones, interferons, bacterial toxins, viral proteins, cytokines, proinsulin, antimicrobial peptides, insecticidal proteins, and enzymes suitable for the production of polyhydroxybutyrate (polyhydroxyalkanoate) polymers.

3. The construct of claim 1 comprising said selectable marker encoding nucleic acid, wherein expression of said marker confers resistance to an agent selected from the group consisting of spectinomycin, streptomycin, kanamycin, hygromycin, glyphosate, bromoxynil, phosphinothricine and sulfonylurea.

4. A plant cell comprising the construct of claim 1.

5. A plant cell plastid comprising the construct of claim 1.

6. A plant, plant seed, plant cell or progeny thereof comprising the construct of claim 2.

7. A method for producing a plant cell which expresses a heterologous protein of interest, said method comprising introducing the construct as claimed in claim 1 into said plant cell.

8. A plant regenerated from a plant cell produced by the method of claim 7.

9. A plant, plant seed, plant cell or progeny thereof comprising the plant cell of claim 4.

10. The construct of claim 1, wherein said at least one heterologous protein is selected from the group consisting of antibodies, hormones, interferons, bacterial toxins, viral proteins, cytokines, proinsulin, antimicrobial peptides, insecticidal proteins, and enzymes suitable for the production of polyhydroxybutyrate (polyhydroxyalkanoate) polymers
   and said selectable marker encoding nucleic acid is present and wherein expression of said marker confers resistance to an agent selected from the group consisting of spectinomycin, streptomycin, kanamycin, hygromycin, glyphosate, bromoxynil, phosphinothricine and sulfonylurea.

11. A plant, plant seed, plant cell or progeny thereof comprising the construct of claim 10.

12. A vector comprising the construct of claim 1, wherein the vector targets insertion of said construct into an intergenic region of the plastid genome and expression of said construct lacks a promoter and expression of said protein occurs via read-through transcription from an endogenous upstream promoter.

13. The vector of claim 12, wherein said intergenic is trnI-trnA region and expression of said construct occurs via read through transcription of the plastid rRNA operon.

14. The construct of claim 1, comprising a promoter element operably linked 5' to the nucleotide segment of a)

* * * * *

SEQUENCE LISTING

```
<160> NUMBER OF SEQ ID NOS: 7

<210> SEQ ID NO 1
<211> LENGTH: 6348
<212> TYPE: DNA
<213> ORGANISM: Artificial Sequence
<220> FEATURE:
<223> OTHER INFORMATION: Synthetic Sequence

<400> SEQUENCE: 1
gggccttgta cacaccgccc gtcacactat gggagctggc catgcccgaa gtcgttacct      60
taaccgcaag gaggggatg  ccgaaggcag ggctagtgac tggagtgaag tcgtaacaag     120
gtagccgtac tggaaggtgc ggctggatca cctccttttc agggagagct aatgcttgtt    180
gggtattttg gtttgacact gcttcacacc cccaaaaaaa agaagggagc tacgtctgag    240
ttaaacttgg agatggaagt cttctttcct ttctcgacgg tgaagtaaga ccaagctcat    300
```

```
gagcttatta tcctaggtcg gaacaagttg ataggacccc cttttttacg tccccatgtt      360 cccccgtgt ggcgacatgg gggcgaaaaa aggaaagaga gggatggggt ttctctcgct       420
tttggcatag cgggccccca gtgggaggct cgcacgacgg gctattagct cagtggtaga      480
gcgcgcccct gataattgcg tcgttgtgcc tgggctgtga gggctctcag ccacatggat      540
agttcaatgt gctcatcggc gcctgaccct gagatgtgga tcatccaagg cacattagca      600
tggcgtactc ctcctgttcg aaccggggtt tgaaaccaaa ctcctcctca ggaggataga      660
tggggcgatt cgggtgagat ccaatgtaga tccaactttc gattcactcg tgggatccgg      720
gcggtccggg ggggaccacc acggctcctc tcttctcgag aatccataca tcccttatca     780
gtgtatggac agctatctct cgagcacagg tttagcaatg gaaaataaaa atggagcacc      840
taacaacgca tcttcacaga ccaagaacta cgagatcgcc cctttcattc tggggtgacg     900
gagggatcgt accattcgag ccgtttttt cttgactcga aatgggagca ggtttgaaaa       960
aggatcttag agtgtctagg gttgggccag gagggtctct taacgccttc ttttttcttc    1020
tcatcggagt tatttcacaa agacttgcca gggtaaggaa aaggggggga acaagcacac    1080
ttggagagcg cagtacaacg gagagttgta tgctgcgttc gggaaggatg aatcgctccc    1140
gaaaaggaat ctattgattc tctcccaatt ggttggaccg taggtgcgat gatttacttc    1200
acgggcgagg tctctggttc aagtccagga tgcccagct gcatttaaat ggcgcgccga     1260
attcgagctc ggtacccggg gatcctctag agtcgacctg caggcatgca agcttgcggc    1320
cgcagtagct tataacttcg tatagcatac attatacgaa gttatagatc cgctcccccg    1380
ccgtcgttca atgagaatgg ataagaggct cgtgggattg acgtgagggg gcagggatgg    1440
ctatatttct gggagaatta accgatcgac gtgcaagcgg acatttattt taaattcgat    1500 aattttgca aaaacatttc gacatattta tttattttat tattatgaga atcaatccta     1560
ctacttctgg ttctggggtt tccacggcta gtagcgaagc ggtgatcgcc gaagtatcga    1620
ctcaactatc agaggtagtt ggcgtcatcg agcgccatct cgaaccgacg ttgctggccg    1680
tacatttgta cggctccgca gtggatggcg gcctgaagcc acacagtgat attgatttgc    1740
tggttacggt gaccgtaagg cttgatgaaa caacgcggcg agctttgatc aacgaccttt    1800
tggaaacttc ggcttcccct ggagagagcg agattctccg cgctgtagaa gtcaccattg    1860
ttgtgcacga cgacatcatt ccgtggcgtt atccagctaa gcgcgaactg caatttggag    1920
aatggcagcg caatgacatt cttgcaggta tcttcgagcc agccacgatc gacattgatc    1980
tggctatctt gctgacaaaa gcaagagaac atagcgttgc cttggtaggt ccagcggcgg    2040
aggaactctt tgatccggtt cctgaacagg atctatttga ggcgctaaat gaaaccttaa    2100
cgctatggaa ctcgccgccc gactgggctg gcgatgagcg aaatgtagtg cttacgttgt    2160
cccgcatttg gtacagcgca gtaaccggca aaatcgcgcc gaaggatgtc gctgccgact    2220
gggcaatgga gcgcctgccg gcccagtatc agcccgtcat acttgaagct agacaggctt    2280
atcttggaca agaagaagat cgcttggcct cgcgcgcaga tcagttggaa gaatttgtcc    2340
actacgtgaa aggcgagatc accaaggtag tgggcaaaga acaaaaactc atttctgaag    2400
aagacttgtg agtctagcta gagcgatcct ggcctagtct ataggaggtt ttgaaaagaa    2460
aggagcaata atcattttct tgttctatca agagggtgct attgctcctt tctttttttc    2520
tttttattta tttactagta ttttacttac atagactttt tgtttacat tatagaaaaa    2580 gaaggagagg ttattttctt gcatttattc atggggatc aaagctgatc tataacttcg    2640
tatagcatac attatacgaa gttatggtac actatttaaa tgcgctccac ttggctcggg    2700
```

```
gggatatagc tcagttggta gagctccgct cttgcaattg ggtcgttgcg attacgggtt    2760
ggatgtctaa ttgtccaggc ggtaatgata gtatcttgta cctgaaccgg tggctcactt    2820
tttctaagta atggggaaga ggaccgaaac gtgccactga agactctac tgagacaaag     2880
atgggctgtc aagaacgtag aggaggtagg atgggcagtt ggtcagatct agtatggatc    2940
gtacatggac ggtagttgga gtcggcggct ctcccagggt tccctcatct gagatctctg    3000
gggaagagga tcaagttggc ccttgcgaac agcttgatgc actatctccc ttcaacccctt   3060
tgagcgaaat gcggcaaaag aaaggaagg aaaatccatg gaccgacccc atcatctcca     3120
ccccgtagga actacgagat caccccaagg acgccttcgg catccagggg tcacggaccg    3180
accatagaac cctgttcaat aagtggaacg cattagctgt ccgctctcag gttgggcagt    3240
cagggtcgga gaagggcaat gactcattct tagttagaat gggattccaa ctcagcacct    3300
tttgagtgag attttgagaa gagttgctct ttggagagca cagtacgatg aaagttgtaa    3360
gctgtgttcg ggggggagtt attgtctatc gttggcctct atggtagaat cagtcggggg    3420
acctgagagg cggtggttta ccctgcggcg gatgtcagcg gttcgagtcc gcttatctcc    3480
aactcgtgaa cttagccgat acaaagctct ggcgtaatag cgaagaggcc cgcaccgatc    3540
gcccttccca acagttgcgc agcctgaatg gcgaatggcg cctgatgcgg tattttctcc    3600
ttacgcatct gtgcggtatt tcacaccgca tacgtcaaag caaccatagt acgcgccctg    3660
tagcggcgca ttaagcgcgg cgggtgtggt ggttacgcgc agcgtgaccg ctacacttgc    3720
cagcgcccta gcgcccgctc ctttcgcttt cttcccttcc tttctcgcca cgttcgccgg    3780
ctttccccgt caagctctaa atcgggggct ccctttaggg ttccgattta gtgctttacg    3840
gcacctcgac cccaaaaaac ttgatttggg tgatggttca cgtagtgggc catcgccctg    3900
atagacggtt tttcgccctt tgacgttgga gtccacgttc tttaatagtg gactcttgtt    3960
ccaaactgga acaacactca accctatctc gggctattct tttgatttat aagggatttt    4020
gccgatttcg gcctattggt taaaaatga gctgatttaa caaaaattta acgcgaattt     4080
taacaaaata ttaacgttta caattttatg gtgcactctc agtacaatct gctctgatgc    4140
cgcatagtta agccagcccc gacacccgcc aacacccgct gacgcgccct gacgggcttg    4200
tctgctcccg gcatccgctt acagacaagc tgtgaccgtc tccgggagct gcatgtgtca    4260
gaggttttca ccgtcatcac cgaaacgcgc gagacgaaag gcctcgtga tacgcctatt     4320
tttataggtt aatgtcatga taataatggt ttcttagacg tcaggtggca cttttcgggg    4380
aaatgtgcgc ggaaccccta tttgtttatt tttctaaata cattcaaata tgtatccgct    4440
catgagacaa taaccctgat aaatgcttca ataatattga aaaggaaga gtatgagtat     4500
tcaacatttc cgtgtcgccc ttattccctt ttttgcggca ttttgccttc ctgttttgc     4560
tcacccagaa acgctggtga agtaaaaga tgctgaagat cagttgggtg cacgagtggg    4620
ttacatcgaa ctggatctca acagcggtaa gatccttgag agttttcgcc ccgaagaacg    4680
ttttccaatg atgagcactt ttaaagttct gctatgtggc gcggtattat cccgtattga    4740
cgccgggcaa gagcaactcg gtcgccgcat acactattct cagaatgact tggttgagta    4800
ttcaccagtc acagaaaagc atcttacgga tggcatgaca gtaagagaat tatgcagtgc    4860
tgccataacc atgagtgata acactgcggc caacttactt ctgacaacga tcggaggacc    4920
gaaggagcta accgcttttt tgcacaacat gggggatcat gtaactcgcc ttgatcgttg    4980
ggaaccggag ctgaatgaag ccataccaaa cgacgagcgt gacaccacga tgcctgtagc    5040
aatggcaaca acgttgcgca aactattaac tggcgaacta cttactctag cttcccggca    5100
```

| | |
|---|---|
| acaattaata gactggatgg aggcggataa agttgcagga ccacttctgc gctcggccct | 5160 |
| tccggctggc tggtttattg ctgataaatc tggagccggt gagcgtgggt ctcgcggtat | 5220 |
| cattgcagca ctggggccag atggtaagcc ctcccgtatc gtagttatct acacgacggg | 5280 |
| gagtcaggca actatggatg aacgaaatag acagatcgct gagataggtg cctcactgat | 5340 |
| taagcattgg taactgtcag accaagttta ctcatatata ctttagattg atttaaaact | 5400 |
| tcatttttaa tttaaaagga tctaggtgaa gatcctttt gataatctca tgaccaaaat | 5460 |
| cccttaacgt gagttttcgt tccactgagc gtcagacccc gtagaaaaga tcaaaggatc | 5520 |
| ttcttgagat ccttttttc tgcgcgtaat ctgctgcttg caaacaaaaa aaccaccgct | 5580 |
| accagcggtg gtttgtttgc cggatcaaga gctaccaact cttttccga aggtaactgg | 5640 |
| cttcagcaga gcgcagatac caaatactgt ccttctagtg tagccgtagt taggccacca | 5700 |
| cttcaagaac tctgtagcac cgcctacata cctcgctctg ctaatcctgt taccagtggc | 5760 |
| tgctgccagt ggcgataagt cgtgtcttac cgggttggac tcaagacgat agttaccgga | 5820 |
| taaggcgcag cggtcgggct gaacgggggg ttcgtgcaca gcccagct tggagcgaac | 5880 |
| gacctacacc gaactgagat acctacagcg tgagctatga aaagcgcca cgcttcccga | 5940 |
| agggagaaag gcggacaggt atccggtaag cggcagggtc ggaacaggag agcgcacgag | 6000 |
| ggagcttcca gggggaaacg cctggtatct ttatagtcct gtcgggttc gccacctctg | 6060 |
| acttgagcgt cgatttttgt gatgctcgtc aggggggcgg agcctatgga aaacgccag | 6120 |
| caacgcggcc ttttacggtt cctggccttt tgctggcctt tttgctcaca tgttctttcc | 6180 |
| tgcgttatcc cctgattctg tggataaccg tattaccgcc tttgagtgag ctgataccgc | 6240 |
| tcgccgcagc cgaacgaccg agcgcagcga gtcagtgagc gaggaagcgg aagagcgccc | 6300 |
| aatacgcaaa ccgcctctcc ccgcgcgttg gccgattcat taatgcag | 6348 |

<210> SEQ ID NO 2
<211> LENGTH: 2277
<212> TYPE: DNA
<213> ORGANISM: Artificial Sequence
<220> FEATURE:
<223> OTHER INFORMATION: Synthetic Sequence

<400> SEQUENCE: 2

| | |
|---|---|
| gaattccgtc gaggtcaacc caaataatgt tttaaaattt taaaaataat gtaggaggaa | 60 |
| aaattatgaa tcaaaataaa cacggaatta ttggcgcttc caattgtggt tgtgcatctg | 120 |
| atgatgttgc gaaatatcct ttagccaaca atccatattc atctgcttta aatttaaatt | 180 |
| cttgtcaaaa tagtagtatt ctcaactgga ttaacataat aggcgatgca gcaaaagaag | 240 |
| cagtatctat tgggacaacc atagtctctc ttatcacagc accttctctt actggattaa | 300 |
| tttcaatagt atatgacctt ataggtaaag tactaggagg tagtagtgga caatccatat | 360 |
| cagatttgtc tatatgtgac ttattatcta ttattgattt acgggtaagt cagagtgttt | 420 |
| taaatgatgg gattgcagat tttaatggtt ctgtactctt atacaggaac tatttagagg | 480 |
| ctctggatag ctggaataag aatcctaatt ctgcttctgc tgaagaactc cgtactcgtt | 540 |
| ttagaatcgc cgactcagaa tttgataaaa ttttaacccg agggtcttta acgaatggtg | 600 |
| gctcgttagc tagacaaaat gcccaaatat tattattacc ttcttttgcg agcgctgcat | 660 |
| ttttccattt attactacta agggatgcta ctagatatgg cactaattgg gggctataca | 720 |
| atgctacacc ttttataaat tatcaatcaa aactagtaga gcttattgaa ctatatactg | 780 |
| attattgcgt acattggtat aatcgaggtt tcaacgaact aagacaacga ggcactagtg | 840 |

```
ctacagcttg gttagaattt catagatatc gtagagagat gacattgatg gtattagata    900
tagtagcatc attttcaagt cttgatatta ctaattaccc aatagaaaca gattttcagt    960
tgagtagggt catttataca gatccaattg gttttgtaca tcgtagtagt cttaggggag   1020
aaagttggtt tagctttgtt aatagagcta atttctcaga tttagaaaat gcaataccta   1080
atcctagacc gtcttggttt ttaaataata tgattatatc tactggttca cttacattgc   1140
cggttagccc aagtactgat agagcgaggg tatggtatgg aagtcgagat cgaatttccc   1200
ctgctaattc acaatttatt actgaactaa tctctggaca acatacgact gctacacaaa   1260
ctattttagg gcgaaatata tttagagtag attctcaagc ttgtaattta aatgatacca   1320
catatggagt gaatagggcg gtattttatc atgatgcgag tgaaggttct caaagatccg   1380
tgtacgaggg gtatattcga acaactggga tagataaccc tagagttcaa aatattaaca   1440
cttatttacc tggagaaaat tcagatatcc caactccaga agactatact catatattaa   1500
gcacaacaat aaatttaaca ggaggactta gacaagtagc atctaatcgc cgttcatctt   1560
tagtaatgta tggttggaca cataaaagtc tggctcgtaa caataccatt aatccagata   1620
gaattacaca gataccattg acgaaggttg atacccgagg cacaggtgtt tcttatgtga   1680
atgatccagg atttatagga ggagctctac ttcaaaggac tgaccatggt tcgcttggag   1740
tattgagggt ccaatttcca cttcacttaa gacaacaata tcgtattaga gtccgttatg   1800
cttctacaac aaatattcga ttgagtgtga atggcagttt cggtactatt tctcaaaatc   1860
tccctagtac aatgagatta ggagaggatt taagatacgg atcttttgct ataagagagt   1920
ttaatacttc tattagaccc actgcaagtc cggaccaaat tcgattgaca atagaaccat   1980
cttttattag acaagaggtc tatgtagata gaattgagtt cattccagtt aatccgacgc   2040
gagaggcgaa agaggatcta gaagcagcaa aaaagcggt ggcgagcttg tttacacgca   2100
caagggacgg attacaagta aatgtgaaag attatcaagt cgatcaagcg gcaaatttag   2160
tgtcatgctt atcagatgaa caatatgggt atgacaaaaa gatgttattg gaagcggtac   2220
gtgcggcaaa acgacttagc cgagaacgca acttacttca ggatccataa ttctaga      2277
```

<210> SEQ ID NO 3
<211> LENGTH: 2307
<212> TYPE: DNA
<213> ORGANISM: Artificial Sequence
<220> FEATURE:
<223> OTHER INFORMATION: Synthetic Sequence

<400> SEQUENCE: 3

```
gaattccgtc gaggtcaacc caaataatgt tttaaaattt taaaaataat gtaggaggaa     60
aaattatgaa tcaaaataaa cacggaatta ttggcgcttc caattgtggt tgtgcatctg    120
atgatgttgc gaaatatcct ttagccaaca atccatattc atctgcttta aatttaaatt    180
cttgtcaaaa tagtagtatt tcaactggaa ttaacataat aggcgatgca gcaaaagaag    240
cagtatctat tgggacaacc atagtctctc ttatcacagc accttctctt actggattaa    300
tttcaatagt atatgacctt ataggtaaag tactaggagg tagtagtgga caatccatat    360
cagatttgtc tatatgtgac ttattatcta ttattgattt acgggtaagt cagagtgttt    420
taaatgatgg gattgcagat tttaatggtt ctgtactctt atacaggaac tatttagagg    480
ctctggatag ctggaataag aatcctaatt ctgcttctgc tgaagaactc cgtactcgtt    540
ttagaatcgc cgactcagaa tttgatagaa ttttaacccg agggtcttta acgaatggtg    600
gctcgttagc tagacaaaat gcccaaatat tattattacc ttcttttgcg agcgctgcat    660
```

```
ttttccattt attactacta agggatgcta ctagatatgg cactaattgg gggctataca    720
atgctacacc ttttataaat tatcaatcaa aactagtaga gcttattgaa ctatatactg    780
attattgcgt acattggtat aatcgaggtt tcaacgaact aagacaacga ggcactagtg    840
ctacagcttg gttagaattt catagatatc gtagagagat gacattgatg gtattagata    900
tagtagcatc attttcaagt cttgatatta ctaattaccc aatagaaaca gattttcagt    960
tgagtagggt catttataca gatccaattg gttttgtaca tcgtagtagt cttaggggag   1020
aaagttggtt tagcttttgtt aatagagcta atttctcaga tttagaaaat gcaatacccta  1080 atcctagacc gtcttggttt ttaaataata tgattatatc tactggttca cttacattgc   1140
cggttagccc aagtactgat agagcgaggg tatggtatgg aagtcgagat cgaatttccc   1200
ctgctaattc acaattttatt actgaactaa tctctggaca acatacgact gctacacaaa  1260
ctattttagg gcgaaatata tttagagtag attctcaagc ttgtaattta aatgatacca   1320
catatggagt gaatagggcg gtattttatc atgatgcgag tgaaggttct caaagatccg   1380
tgtacgaggg gtatattcga acaactggga tagataaccc tagagttcaa aatattaaca   1440
cttatttacc tggagaaaat tcagatatcc caactccaga agactatact catatattaa   1500
gcacaacaat aaatttaaca ggaggactta dacaagtagc atctaatcgc cgttcatctt   1560
tagtaatgta tggttggaca cataaaagtc tggctcgtaa caataccatt aatccagata   1620
gaattacaca gataccattg acgaaggttg ataccccgagg cacaggtgtt tcttatgtga   1680
atgatccagg atttataggg ggagctctac ttcaaaggac tgaccatggt tcgcttggag   1740
tattgagggt ccaatttcca cttcacttaa gacaacaata tcgtattaga gtccgttatg   1800
cttctacaac aaatattcga ttgagtgtga atggcagttt cggtactatt tctcaaaatc   1860
tccctagtac aatgagatta ggagaggatt taagatacgg atcttttgct ataagagagt   1920
ttaatacttc tattagaccc actgcaagtc cggaccaaat tcgattgaca atagaaccat   1980
cttttattag acaagaggtc tatgtagata gaattgagtt cattccagtt aatccgacgc   2040
gagaggcgaa agaggatcta gaagcagcaa aaaaagcggt ggcgagcttg tttacacgca   2100
caagggacgg attacaagta aatgtgaaag attatcaagt cgatcaagcg gcaaatttag   2160
tgtcatgctt atcagatgaa caatatgggt atgacaaaaa gatgttattg gaagcggtac   2220
gtgcggcaaa acgacttagc cgagaacgca acttacttca ggatccagaa caaaaactca   2280
tttctgaaga agacttgtga ttctaga                                       2307

<210> SEQ ID NO 4
<211> LENGTH: 89
<212> TYPE: DNA
<213> ORGANISM: Artificial Sequence
<220> FEATURE:
<223> OTHER INFORMATION: Synthetic Sequence

<400> SEQUENCE: 4
gctgcattta aatggcgcgc cgaattccgt cgaggtcaac ccaaataatg ttttaaaatt     60
ttaaaaataa tgtaggagga aaattatg                                       89

<210> SEQ ID NO 5
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 5
```

```
Glu Gln Lys Leu Ile Ser Glu Glu Asp Leu
 1               5                  10

<210> SEQ ID NO 6
<211> LENGTH: 46
<212> TYPE: DNA
<213> ORGANISM: Artificial Sequence
<220> FEATURE:
<223> OTHER INFORMATION: Synthetic Sequence

<400> SEQUENCE: 6
ggatccgaac aaaaactcat ttctgaagaa gacttgtgat tctaga                    46

<210> SEQ ID NO 7
<211> LENGTH: 49
<212> TYPE: DNA
<213> ORGANISM: Artificial Sequence
<220> FEATURE:
<223> OTHER INFORMATION: Synthetic Sequence

<400> SEQUENCE: 7
aacccaaata atgttttaaa attttaaaaa taatgtagga ggaaaaatt                 49
```